(12) United States Patent
Allen et al.

(10) Patent No.: US 7,326,731 B2
(45) Date of Patent: Feb. 5, 2008

(54) MUSCARINIC AGONISTS

(75) Inventors: Jennifer Rebecca Allen, Indianapolis, IN (US); Stephen Andrew Hitchcock, Carmel, IN (US); James Andrew Jamison, Indianapolis, IN (US); Bin Liu, Fishers, IN (US); William Wilson Turner, Jr., Bloomington, IN (US)

(73) Assignee: Eli Lilly and Company, Indianapolis, IN (US)

( * ) Notice: Subject to any disclaimer, the term of this patent is extended or adjusted under 35 U.S.C. 154(b) by 182 days.

(21) Appl. No.: 10/488,519

(22) PCT Filed: Sep. 9, 2002

(86) PCT No.: PCT/US02/25969

§ 371 (c)(1),
(2), (4) Date: Mar. 3, 2004

(87) PCT Pub. No.: WO03/027061

PCT Pub. Date: Apr. 3, 2003

(65) Prior Publication Data

US 2004/0242584 A1   Dec. 2, 2004

(51) Int. Cl.
*A61K 31/16* (2006.01)
*C07C 233/00* (2006.01)

(52) U.S. Cl. .................... 514/613; 564/161

(58) Field of Classification Search ............ 564/161, 564/314; 514/613, 247, 255.06, 256; 544/224; 546/314; 549/83
See application file for complete search history.

(56) References Cited

U.S. PATENT DOCUMENTS

| 6,211,364 | B1 * | 4/2001 | Huff et al. ............... 544/106 |
| 6,395,735 | B2 * | 5/2002 | Hollinshead et al. .... 514/237.8 |
| 6,429,317 | B1 * | 8/2002 | Hollinshead et al. ....... 548/566 |

FOREIGN PATENT DOCUMENTS

| WO | WO 98 31660   | 7/1998 |
| WO | WO 99 04778 A | 2/1999 |

OTHER PUBLICATIONS

Friedman Ji, "Cholinergic targets for cognitive enhancement in schizophrenia: focus on cholinesterase inhibitors and muscarinic agonists," *Psychopharmacology*, (2004), 174:45-53.
Shannon He et al., "Xanomeline, an M1/M4 preferring muscarinic cholinergic receptor agonist, produces antipsychotic-like activity in rats and mice," *Schizophrenia Research*, (2000), 42:249-259.

* cited by examiner

*Primary Examiner*—Rebecca Anderson
*Assistant Examiner*—Susannah Chung
(74) *Attorney, Agent, or Firm*—Tina M. Tucker; Danica Lee Hostettler; R. Craig Tucker

(57) ABSTRACT

The present invention relates to compounds of Formula I: Formula I which are agonists of the M-1 muscarinic receptor.

14 Claims, No Drawings

MUSCARINIC AGONISTS

The present invention relates to the field of pharmaceutical and organic chemistry and provides compounds that are active at the muscarinic receptors.

The compounds of the present invention are muscarinic agonists. More specifically, the compounds of the present invention are selective agonists of the muscarinic M-1 receptor. As such, they are useful for treating a variety of disorders of the central nervous system and other body systems. These disorders include cognitive disorders, ADHD, obesity, Alzheimer's disease, psychoses including schizophrenia, and for alleviation of intraocular pressure such as that found in glaucoma.

Certain indane-like compounds are described as useful for treating conditions associated with malfunctioning of the muscarinic cholinergic system in PCT Publication Nos. WO 97/25983, published 24 Jul. 1997, and WO 99/04778, published 4 Feb.1999.

The present invention provides compounds of Formula I:

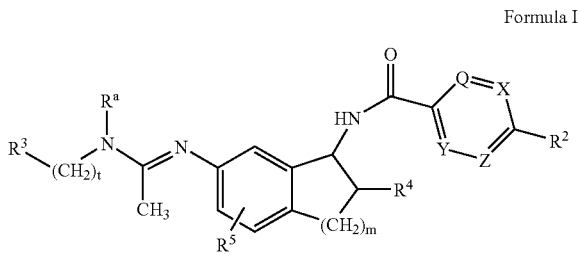

Formula I wherein

Q, X, Y, and Z are independently selected from the group consisting of $CR^1$ and N, provided that no more than two of Q, X, Y, and Z are N and at least two of Q, X, Y, and Z are CH; or Y is CH, Z is CH, and the moiety "Q=X" represents "S" to form a thiophene ring;

$R^1$ is independently at each occurrence selected from the group consisting of hydrogen, halogen, $C_1$-$C_4$ alkoxy, and $C_1$-$C_4$ alkyl;

$R^2$ is selected from the group consisting of halogen; $C_1$-$C_4$ alkoxy; $C_1$-$C_4$ alkyl; $C_3$-$C_8$ cycloalkyl; cyano; trifluoromethyl; pyridinyl optionally substituted with one to two substituents independently selected from the group consisting of halogen, $C_1$-$C_4$ alkoxy, and $C_1$-$C_4$ alkyl; thienyl optionally substituted with one substituent selected from the group consisting of halogen, $C_1$-$C_4$ alkoxy, and $C_1$-$C_4$ alkyl; phenyl optionally substituted with from one to three substituents independently selected from the group consisting of halogen, $C_1$-$C_4$ alkoxy, $C_1$-$C_4$ alkyl, trifluoromethyl, and cyano; and pyrrolyl optionally substituted with one to two substituents independently selected from the group consisting of halogen, $C_1$-$C_4$ alkoxy, and $C_1$-$C_4$ alkyl;

$R^3$ is selected from the group consisting of phenyl optionally substituted with one to three substituents independently selected from the group consisting of halogen, $C_1$-$C_4$ alkoxy, $C_1$-$C_4$ alkyl, trifluoromethyl, cyano, and nitro; naphthyl optionally substituted with one to three substituents independently selected from the group consisting of halogen, $C_1$-$C_4$ alkoxy, $C_1$-$C_4$ alkyl, trifluoromethyl, cyano, and nitro; heteroaryl optionally substituted with one or two substituents independently selected from the group consisting of halogen, $C_1$-$C_4$ alkoxy, and $C_1$-$C_4$ alkyl; or 1,3-benzodioxolyl optionally substituted with one substituent selected from the group consisting of halogen, $C_1$-$C_4$ alkoxy, and $C_1$-$C_4$ alkyl;

$R^4$ is selected from the group consisting of hydrogen, hydroxy, and fluoro;

$R^5$ is selected from the group consisting of hydrogen, halogen, $C_1$-$C_4$ alkoxy, and $C_1$-$C_4$ alkyl;

$R^a$ is selected from the group consisting of hydrogen and methyl;

t is one, two, or three; and m is one or two;

or pharmaceutically acceptable addition salts thereof.

The present invention also provides pharmaceutical compositions, comprising a compound of Formula I and a pharmaceutically acceptable diluent.

Because the compounds of Formula I are agonists of the M-1 muscarinic receptor, the compounds of Formula I are useful for the treatment of a variety of disorders associated with muscarinic receptors, including: cognitive disorders (including age-related cognitive disorder, mild cognitive impairment, cognitive impairment associated with schizophrenia, and chemotherapy-induced cognitive impairment), ADHD, mood disorders (including depression, mania, bipolar disorders), psychosis (in particular schizophrenia), dementia (including Alzheimer's disease, AIDS-induced dementia, vascular dementia, and dementia lacking distinctive histology), Parkinson's disease, and Huntington's Chorea. Also, the present compounds are useful for treating chronic colitis, including Crohn's disease. Additionally, the present compounds are useful for the treatment of pain (including acute pain and chronic pain), xerostomia (dry mouth), Lewy body disease (including diffuse Lewy body disease), aphasia (including primary aphasia and primary aphasia syndromes), and hypotensive syndromes.

In another embodiment the present invention provides methods of treating disorders associated with muscarinic receptors, comprising: administering to a patient in need thereof an effective amount of a compound of Formula I. That is, the present invention provides for the use of a compound of Formula I or a pharmaceutical composition thereof for the manufacture of a medicament for the treatment of disorders associated with muscarinic receptors. The present invention also provides a compound of Formula I for use in therapy.

As used herein, the following terms have the meanings indicated:

The term "halogen" refers to a chloro, fluoro, bromo or iodo atom.

The term "$C_1$-$C_4$ alkyl" refers to a straight or branched alkyl chain having from one to four carbon atoms, and includes methyl, ethyl, n-propyl, iso-propyl, n-butyl, sec-butyl, iso-butyl, and t-butyl. The term "$C_3$-$C_8$ cycloalkyl" refers to cyclopropyl, cyclobutyl, cyclopentyl, cyclohexyl, cycloheptyl, and cyclooctyl.

The term "$C_1$-$C_4$ alkoxy" refers to a straight or branched alkyl chain having from one to four carbon atoms attached to an oxygen atom, and includes methoxy, ethoxy, n-propoxy, iso-propoxy, n-butoxy, iso-butoxy, sec-butoxy, and t-butoxy.

The term "heteroaryl" is taken to mean a stable unsaturated five- or six-membered ring containing from 1 to 2 heteroatoms selected from the group consisting of nitrogen, oxygen and sulfur. Examples of heteroaryl include pyridinyl, pyrimidinyl, pyrazinyl, pyrrolyl, oxazolyl, isoxazolyl, imidazolyl, thiazolyl, pyridazinyl, furyl, thienyl, and the like. Preferred heteroaryl groups are thienyl, pyridinyl, and furyl.

The compounds of the present invention form pharmaceutically acceptable acid addition salts with a wide variety of organic and inorganic acids and include the physiologically acceptable salts which are often used in pharmaceutical chemistry. Such salts are also part of this invention. A "pharmaceutically-acceptable addition salt" is formed from a pharmaceutically-acceptable acid as is well known in the art. Such salts include the pharmaceutically acceptable salts listed in *Journal of Pharmaceutical Science*, 66, 2-19 (1977) which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-di carboxylate, caprate, capryl ate, cinnamate, citrate, form ate, fumarate, glycol late, heptanoate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethyl sulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

The present invention includes the stereoisomers and tautomers of the compounds of Formula I. Herein, the Cahn-Prelog-Ingold designations of (R)- and (S)- and the cis and trans designation of relative stereochemistry are used to refer to specific isomers and relative stereochemistry.

As with any group of pharmaceutically active compounds, some groups are preferred in their end use application. The following paragraphs define preferred classes.

a) When $R^4$ is not hydrogen, compounds which have trans stereochemistry at the 1- and 2-position are preferred.
b) When $R^4$ is not hydrogen, compounds which have the trans stereochemistry at the 1- and 2-position shown below are more preferred.

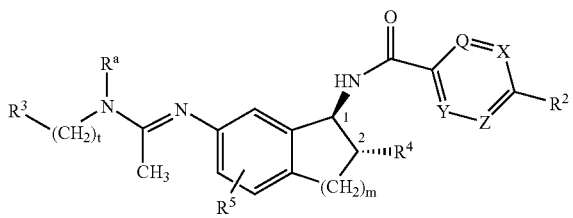

c) $R^a$ is methyl.
d) $R^5$ is hydrogen.
e) $R^4$ is hydroxy.
f) t is one.
g) m is one.
h) $R^a$ is methyl, $R^5$ is hydrogen, $R^4$ is hydroxy, t is one, and m is one.
i) Q, X, Y, and Z are each $CR^1$ provided that at least two of Q, X, Y, and Z are CH.
j) $R^1$ is hydrogen.
k) $R^1$ is halogen.
l) $R^1$ is fluoro.
m) Q, X, Y, and Z are each CH.
n) One of Q, X, Y, and Z is CF and the others are CH.
o) Q is CF and X, Y, and Z are each CH.
q) $R^2$ is phenyl optionally substituted with from one to three substituents independently selected from the group consisting of halogen, $C_1$-$C_4$ alkoxy, $C_1$-$C_4$ alkyl, trifluoromethyl, and cyano.
r) $R^2$ is phenyl.
s) $R^3$ is phenyl optionally substituted with one to three substituents independently selected from the group consisting of halogen, $C_1$-$C_4$ alkoxy, $C_1$-$C_4$ alkyl, trifluoromethyl, cyano, and nitro.
t) $R^3$ is phenyl substituted with one substituent selected from the group consisting of halogen, trifluoromethyl, cyano, or nitro.
u) $R^3$ is phenyl substituted once with halogen.
v) $R^3$ is phenyl substituted once with fluoro.
w) $R^3$ is phenyl substituted once with fluoro in the para-position.
x) $R^2$ is phenyl, $R^3$ is phenyl substituted once with fluoro in the para-position, and Q, X, Y, and Z are each CH.
y) $R^2$ is phenyl, $R^3$ is phenyl substituted once with fluoro in the para-position, Q is CF, and X, Y, and Z are each CH.
z) $R^a$ is methyl, $R^5$ is hydrogen, $R^4$ is hydroxy, t is one, m is one, $R^2$ is phenyl, and Q, X, Y, and Z are each CH.
aa) $R^a$ is methyl, $R^5$ is hydrogen, $R^4$ is hydroxy, t is one, m is one, $R^2$ is phenyl, Q is CF, and X, Y, and Z are each CH.
bb) $R^a$ is methyl, $R^5$ is hydrogen, $R^4$ is hydroxy, t is one, m is one, and $R^3$ is phenyl substituted once with fluoro in the para-position.

The preceding paragraphs may be combined to define additional preferred classes of compounds.

The compounds of Formula I in which $R^4$ is hydroxy are prepared by procedures described in Scheme A. In Scheme A all substituents, unless otherwise indicated, are as previously defined, and all reagents are well known and appreciated in the art.

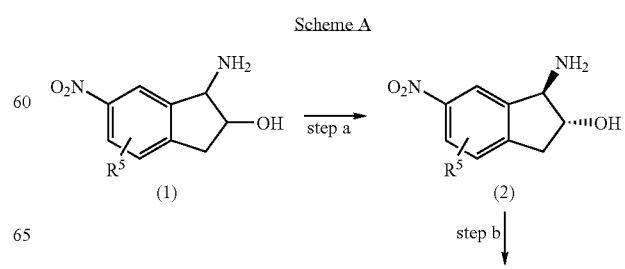

Scheme A

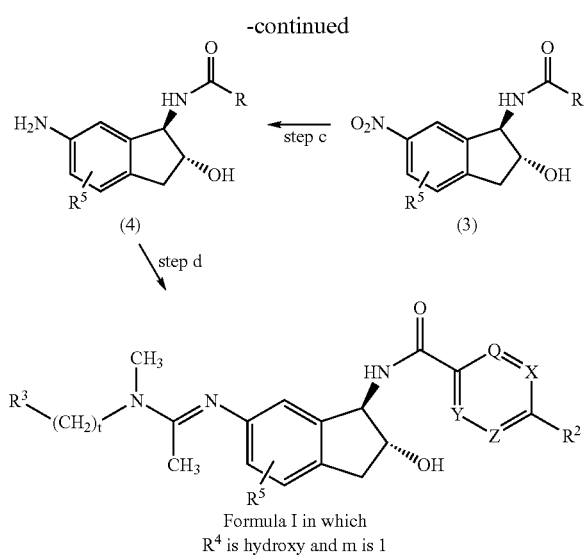

Formula I in which
R⁴ is hydroxy and m is 1

In Scheme A, step a, the compound of Formula (1) is resolved to give a substantially pure compound of Formula (2). The compound of Formula (1) is readily prepared by methods well known and appreciated in the art, such as those found in PCT Publication Nos. WO 97/25983, published 24 Jul. 1997; and WO 99/04778, published 4 Feb. 1999. As used herein the term "substantially pure" refers to enantiomeric purity. The desired stereochemistry in final compounds of Formula 1 may be conveniently introduced in Scheme A, step a, by resolution of compounds of Formula (1). Further processing of resolved compounds of Formula (1), via steps b, c, d, and optional step e, described infra, will result in substantially pure compounds of Formula I. Substantially pure compounds of Formula I can be prepared which are greater than 80%, preferably greater than 90%, more preferably greater than 95%, most preferably greater than 97% enantiomerically pure. The compound of Formula (1) can be resolved by chiral chromatography or by fractional crystallization of diastereomeric acid addition salts. It is expected that a wide variety of such salts are suitable for this purpose. In practice, isomers of mandelic acid have been found to be particularly useful.

For example, the compound of Formula (1) is contacted with the selected acid. Generally, from about 0.4 molar equivalents to a large excess of the selected acid can be used with about 0.4 to 1.5 molar equivalents being preferred and with about 0.5 to 1.1 molar equivalents being more preferred. The resolution is typically carried out by crystallizing the acid addition salt from a solution. In particular, solvents such as lower alcohols, including methanol are useful. It may be advantageous to use small amounts of water with the selected solvent(s) in order to carry out the resolution in a reasonable volume. The use of an anti-solvent may also be advantageous. As used herein, the term "anti-solvent" refers to a solvent in which the salt is significantly less soluble compared to the other selected solvent(s). Preferably, when an anti-solvent is used it is miscible with the other selected solvent(s). Suitable anti-solvents include ethers, such as diethyl ether, methyl t-butyl ether, and the like, and lower alkyl acetates, such as methyl acetate, ethyl acetate, isopropyl acetate, propyl acetate, iso-butyl acetate, sec-butyl acetate, butyl acetate, amyl acetate, iso-amyl acetate, and the like, and alkanes, such as pentane, hexane, heptane, cyclohexane, and the like. When the racemic mixture is used, care should be taken in using an anti-solvent to avoid crystallization of the salt of the undesired diastereomeric salt.

Typically, the crystallization is carried out at initial temperatures of about 40° C. to reflux temperature of the selected solvent(s). The mixture is then cooled to give the salt. Seeding may be advantageous. Preferably the crystallization solution is cooled slowly. The crystallization is most conveniently cooled to temperatures of ambient temperature to about −20° C. The salt can be collected using techniques that are well known in the art, including filtration, decanting, centrifuging, evaporation, drying, and the like. The compound of Formula (2) can be used directly as the acid addition salt of the selected acid. Alternately, before use the compound of Formula (2) can be isolated as another acid addition salt after acid exchange or can by isolated as the base by extraction under basic conditions as is well known and appreciated in the art.

As is readily apparent to one skilled in the art the depicted compound of Formula (2) is of the trans configuration at the 1- and 2-positions of the indane nucleus. Cis compounds are readily prepared from such trans compounds by protection of the amine, inversion of the hydroxy center, followed by deprotection as needed. There are numerous methods which allow for inversions of hydroxy centers, such as by Mitsunobu reaction with suitable carboxylic acids, including acetic acid and benzoic acid, followed by hydrolysis.

Reaction Scheme A, step b, depicts the formation of a compound of Formula (3). It is understood that the compound of Formula (3) can be one in which R is a group as desired in the final product of Formula I as defined above. R may also combine with the carbonyl to form a protecting group, such as t-BOC, which can be later removed before incorporation of an R group as desired in the final product of Formula I. The selection and use of suitable protecting groups is well known and appreciated in the art (Protecting Groups in Organic Synthesis, Theodora Greene (Wiley-Interscience)).

For example, where R is a group as desired in the final product, the coupling reaction depicted in step b is carried out using the appropriate acid or the acid halide derived therefrom. Appropriate acids include various substituted benzoic acids and acid halides, heteroaryl acids and acid halides, and various biaryl carboxylic acids and acid halides. Examples include biphenyl carboxylic acid and 3-fluorobiphenyl-4-carboxylic acid.

For example, the compound of Formula (2) is contacted with an appropriate acid to give a compound of Formula (3). Such coupling reactions are common in peptide synthesis and synthetic methods used therein can be employed. For example, well known coupling reagents, such as resin-bound reagents and carbodiimides with or without the use of well-known additives such as N-hydroxysuccinimide, 1-hydroxybenzotriazole, etc. can be used to facilitate this acylation. The reaction is conventionally conducted in an inert aprotic polar diluent such as dimethylformamide (DMF), methylene chloride (dichloromethane), chloroform, acetonitrile, tetrahydrofuran (THF), and the like. Typically the reaction is carried out at temperatures of from about 0° C. to about 60° C. and typically require from about 1 to about 24 hours. Upon reaction completion, the product of Formula (3) is recovered by conventional methods including extraction, precipitation, chromatography, filtration, trituration, crystallization and the like.

Alternatively, for example, the compound of Formula (2) is contacted with an acid halide of an appropriate acid to give a compound of Formula (3). Such acid halides are commercially available or readily prepared from the corresponding acids by methods well known in the art, such as by the action of phosphorous trichloride, phosphorous tribromide, phosphorous oxychloride, phosphorous pentachloride, thionyl chloride, thionyl bromide, or oxalyl chloride, with or without a small amount of dimethylformamide, in an inert solvent such as, toluene, methylene chloride, or chloroform; at temperatures of from about 0-80° C. The reaction is typically carried out for a period of time ranging from 1 hour to 24 hours. The acid halide can be isolated and purified or can often be used directly, that is, with or without isolation and/or purification. The coupling reactions generally use a suitable base to scavenge the acid generated during the reaction. Suitable bases include, by way of example, sodium hydroxide, potassium hydroxide, pyridine, triethylamine, N,N-diisopropylethylamine, N-methylmorpholine, and the like. The reaction is conventionally conducted in a solvent such as methylene chloride, chloroform, tetrahydrofuran and the like, or under Schotten-Baumann conditions in a solvent mixture such as methylene chloride, ethyl acetate, toluene and water. Typically the coupling reaction is carried out at temperatures of from about −20° C. to about 80° C. and typically require from about 1 to about 24 hours. Upon reaction completion, the product of Formula (3) is recovered by conventional methods including extraction, precipitation, chromatography, filtration, trituration, crystallization and the like.

Reaction Scheme A, step c, depicts the reduction of a nitro group to give a compound of Formula (4). Such reductions can be carried out by a variety of methods that are well known in the art.

For example, a compound of Formula (3) may be hydrogenated over a catalyst, such as palladium-on-carbon, to give a compound of Formula (4). Such hydrogenations are generally carried out in a solvent and a variety of solvents are suitable, for example methanol, ethanol, isopropanol, tetrahydrofuran, or ethyl acetate or mixtures thereof. The hydrogenation may be performed at an initial hydrogen pressure of 20-180 psi (137-1241 kPa). The reaction is typically carried out at temperature of about 0° C. to about 60° C. The reaction typically requires 1 hour to 3 days. The product can be isolated and purified by techniques well known in the art, such as filtration, extraction, evaporation, trituration, precipitation, chromatography, and recrystallization.

In Scheme A, step d, a compound of Formula (4) is contacted with an appropriate amidine forming agent to give a compound of Formula I. Appropriate amidine forming agents include 1-methylthio-1-methyl-N-(4-fluorobenzyl)-N-methylimmonium triflate and 1-methylthio-1-methyl-N-(4-fluorobenzyl)-N-methylimmonium iodide. One of ordinary skill in the art will recognize that appropriate amidine forming agents may be prepared in advance or in situ if desired.

For example, a compound of Formula (4) is contacted with from about 1-3 equivalents of an appropriate amidine forming agent. The reaction is generally carried out in a dry solvent such as methylene chloride, toluene, or tetrahydrofuran at temperatures of from about −20° C. to 50° C. The reaction is carried out using an appropriate base such as pyridine, collidine, or triethylamine. The reaction typically requires 1 to 18 hours. The product can be isolated and purified by techniques well known in the art, such as quenching, filtration, extraction, evaporation, trituration, precipitation, chromatography, and recrystallization.

As will be readily appreciated, where R is a protecting group introduced in step b, the protecting group can be removed after step d and the resulting amine coupled with an appropriate acid or acid halide as also described above in step b to give a compound of Formula I.

Some compounds of Formula I are intermediates for other final compounds of Formula I. For example, when $R^2$ is iodo, another reagent, for example, 2-(tributylstannyl) thiophene or 2-(tributylstannyl)pyridine, may be used to displace iodo as a leaving group and substitute a different $R^2$ group as desired in the final product.

In Scheme A, optional step e, not shown, an acid addition salt of a compound of Formula I is formed using a pharmaceutically-acceptable acid. The formation of acid addition salts is well known and appreciated in the art.

The compounds of Formula I in which $R^4$ is hydrogen are prepared from compounds of Formula (3) or from amine protected compounds of Formula (2) by deoxygenation. Such deoxygenation reactions are readily carried out using procedures well known in the art, described, for example, by Larock, Comprehensive Organic Transformations, pg. 44-52 (1999). Alternately, the compounds of Formula I in which $R^4$ is hydrogen are prepared by procedures described in Scheme B. In Scheme B all substituents, unless otherwise indicated, are as previously defined, and all reagents are well known and appreciated in the art.

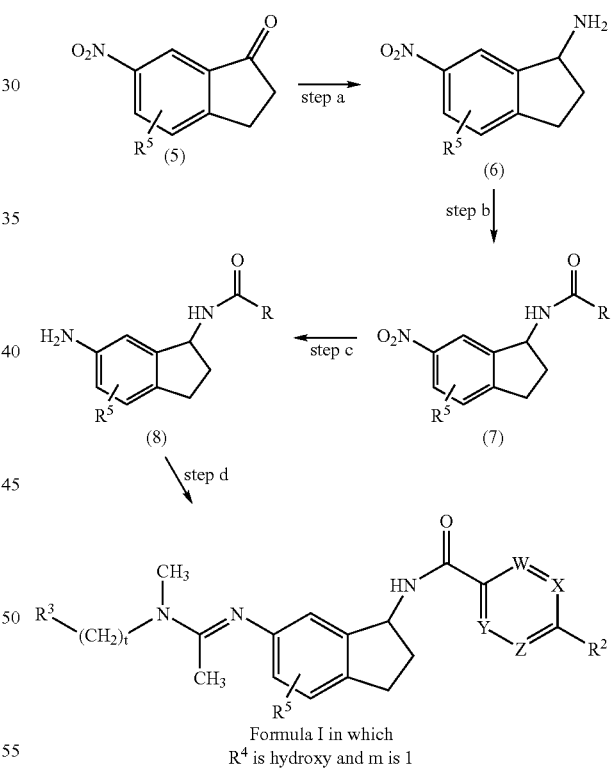

Reaction Scheme B, step a, depicts the reductive amination of a compound of Formula (5) to give a compound of Formula (6). Such reductive aminations are carried out under a variety of conditions. The reaction depicted in Scheme B, step a, can be carried out using ammonia or a protected amine, such as benzyl amine, dibenzyl amine, and the like followed by deprotection to give the compound of Formula (6).

For example, a compound of Formula (5) is reacted with an excess of ammonia and sodium cyanoborohydride to give a compound of Formula (6). As is well known in the art, it may be advantageous to monitor and adjust the pH during such reactions. The reaction is carried out in a solvent, such as methanol, ethanol, isopropanol, and water or mixtures thereof. Typically the reaction is carried out at temperatures of from about 0° C. to about 60° C. and typically require from about 1 to about 24 hours. Upon reaction completion, the product of Formula (6) is recovered by conventional methods including extraction, precipitation, chromatography, filtration, trituration, crystallization, and the like.

Reaction Scheme B, steps b, c, d, and optional step e, are carried out by the methods described in Scheme A, steps b, c, d, and optional step e, to give a compound of Formula I.

The compounds of Formula I in which $R^4$ is fluoro are prepared from compounds of Formula (3) or from amine protected compounds of Formula (2) by halogenation procedures well known in the art, described, for example, by Larock, Comprehensive Organic Transformations, pg. 689-701 (1999).

The present invention is further illustrated by the following examples and preparations. These examples and preparations are illustrative only and are not intended to limit the invention in any way.

The terms used in the examples and preparations have their normal meanings unless otherwise designated. For example, "° C." refers to degrees Celsius; "M" refers to molar or molarity; "mmol" refers to millimole or millimoles; "g" refers to gram or grams; "mL" refers to milliliter or milliliters; "mp" refers to melting point; "brine" refers to a saturated aqueous sodium chloride solution; etc. In the $^1$H NMR, all chemical shifts are given in δ, unless otherwise indicated.

Coupling Procedures

Method A

2'-Chlorobiphenyl-4-carboxylic acid

Combine methyl-4-bromobenzoate (1.0 g, 4.65 mmol), 2-chlorophenylboronic acid (799 mg, 5.1 mmol), Pd(OAc)$_2$ (51 mg, 0.46 mmol) and sodium carbonate (1.5 g, 13.9 mmol) in DMF (20 mL) and water (2.0 mL) with stirring. Purge the reaction mixture with argon, add triphenylphosphine (61 mg, 0.23 mmol) and purge again with argon. Place the sealed reaction in an oil bath maintained at 80° C. and allow to stir for 1 hour. Cool the reaction to room temperature, dilute with ethyl acetate and filter through a short plug of celite with additional ethyl acetate. Wash the organics with water, dry over MgSO$_4$, filter and evaporate. Purification by flash column chromatography yields 2'-chlorobiphenyl-4-carboxylic acid methyl ester as a yellow solid. Dissolve the purified ester in THF (0.25M) and add an equal volume of 1M NaOH. Stir vigorously at room temperature for 15 hours. Upon completion, acidify the reaction with conc. HCl and extract with ethyl acetate. Evaporation of the solvent yields 762 mg (67%) of the title compound. MS (m/e): 231.1 (M$^-$).

The following compounds are prepared essentially as described above.

| | |
|---|---|
| 6-(2-Chlorophenyl)pyridine-3-carboxylic acid | MS 233.9 (MH$^+$) |
| 6-(2,4-Difluorophenyl)pyridine-3-carboxylic acid | MS 235.9 (MH$^+$) |
| 6-Phenylpyridine-3-carboxylic acid methyl ester | MS 214.1 (MH$^+$) |
| 6-(2-Methylphenyl)pyridine-3-carboxylic acid | MS 214.0 (MH$^+$) |
| 2'-Trifluoromethylbiphenyl-4-carboxylic acid | MS 265.2 (M$^-$) |

-continued

| | |
|---|---|
| 2-Methylbiphenyl-4-carboxylic acid | MS 211.3 (M$^-$) |
| 3-Fluorobiphenyl-4-carboxylic acid | MS 215.1 (M$^-$) |
| 2',6'-Dichlorobiphenyl-4-carboxylic acid | MS 264.9 (M$^-$) |
| 2',6'-Difluorobiphenyl-4-carboxylic acid | MS 233.1 (M$^-$) |
| 2'-Methoxybiphenyl-4-carboxylic acid | MS 227.0 (M$^-$) |
| 3,4'-Difluorobiphenyl-4-carboxylic acid | MS 233.1 (M$^-$) |
| 3,2'-Difluorobiphenyl-4-carboxylic acid | MS 233.1 (M$^-$) |
| 3-Chlorobiphenyl-4-carboxylic acid | MS 231.1 (M$^-$) |
| 4-(Thien-2-yl)phenyl-1-carboxylic acid | MS 203.1 (M$^-$) |
| 4'-Fluorobiphenyl-4-carboxylic acid (Hydrolysis in dioxane at 60° C.) | MS 214.9 (M$^-$) |
| 3'-Fluorobiphenyl-4-carboxylic acid (Hydrolysis in dioxane) | MS 215.0 (M$^-$) |
| 3'-Cyanobiphenyl-4-carboxylic acid (Hydrolysis with LiOH in dioxane) | MS 222.0 (M$^-$) |

Method B

5-Phenylpyrazine-2-carboxylic acid

Combine 5-chloropyrazine-2-carboxylic acid methyl ester (626 mg, 3.64 mmol), phenylboronic acid (666 mg, 5.45 mmol), cesium fluoride (55 mg, 0.36 mmol) and Na$_2$CO$_3$ (964 mg, 9.09 mmol) in DMF (5 mL) and water (5 mL) with stirring. Place the heterogeneous reaction mixture, open to the air, in an oil bath maintained at 80° C. After 5 minutes of heating, add Pd(OAc)$_2$ (81 mg 0.36 mmol) in one portion and stir until reaction turns black. Cool the reaction to room temperature, dilute with ethyl acetate, and filter through a short plug of celite with additional ethyl acetate. Wash the organics with water, dry over MgSO$_4$, filter and evaporate. Purification by flash column chromatography yields 2-phenylpyrimidine-5-carboxylic acid methyl ester as a yellow solid. Dissolve the purified ester in THF (0.25M) and add an equal volume of 1M NaOH. Stir vigorously at room temperature for 15 hours. Upon completion, acidify the reaction with conc. HCl and extract with ethyl acetate. Evaporation of the solvent yields 63 mg (8%) of the title compound. $^1$H NMR (DMSO): 9.37 (s, 1H), 9.21 (s, 1H), 8.23-8.21 (m, 2H), 7.57-7.77 (m, 3H).

The following compounds are prepared essentially as described above.

| | |
|---|---|
| 2'-Fluoro-6'-trifluoromethylbiphenyl-4-carboxylic acid | MS 283.1 (M$^-$) |
| 3,2',4'-Trifluorobiphenyl-4-carboxylic acid | MS 251.1 (M$^-$) |
| 4'-Fluoro-2'-methoxybiphenyl-4-carboxylic acid | MS 245.1 (MH$^-$) |
| 3-Chloro-2',4'-difluorobiphenyl-4-carboxylic acid | MS 267.1 (M$^-$) |
| 4'-Fluoro-2'-methylbiphenyl-4-carboxylic acid | MS 229.0 (M$^-$) |
| 4'-Trifluoromethylbiphenyl-4-carboxylic acid | MS 265.1 (M$^-$) |
| 2-Fluoro-4-(thien-2-yl)phenyl-1-carboxylic acid | MS 221.1 (M$^-$) |

Method C

3',4'-Difluorobiphenyl-4-carboxylic acid

Combine 3,4-difluorobenzeneboronic acid (1.0 g, 5.2 mmol), methyl-4-bromobenzoate (0.241 g, 1.73 mmol), Pd(OAc)$_2$ (0.019 g, 0.086 mmol), tetrabutylammonium bromide (0.111 g, 0.345 mmol), and potassium phosphate (0.733 g, 3.454 mmol). Purge the reaction vessel with argon and add anhydrous DMF (20 ml) to the reaction mixture. Heat the sealed reaction vessel to 120° C. with stirring until completion. Cool the reaction to room temperature, dilute with ethyl acetate, and filter through a short plug of celite with additional ethyl acetate. Wash organics with water, dry over MgSO₄, filter, and evaporate. Purification by flash column chromatography yields 3',4'-difluorobiphenyl-4-carboxylic acid methyl ester as a yellow solid. Dissolve the purified ester in dioxane (45 ml) and add an equal volume of 1 M aqueous NaOH. Heat the reaction vessel to 60° C. with stirring until completion. Remove the solvent by evaporation. Dissolve the residue in dichloromethane and wash with 1N aqueous hydrochloric acid. Dry the organics over MgSO₄, filter and evaporate to yield 0.048 g (12%) of the title compound. MS (m/e): 235 (M⁺).

The following compounds are prepared essentially as described above.

| | |
|---|---|
| 6-(2-Fluorophenyl)pyridine-3-carboxylic acid | MS 218.0 (MH⁺) |
| 3',5'-Dimethylbiphenyl-4-carboxylic acid | MS 225.0 (M⁻) |
| 3',5'-Difluorobiphenyl-4-carboxylic acid | MS 233.0 (M⁻) |
| 3',5'-Dichlorobiphenyl-4-carboxylic acid | MS 267.1 (M⁺) |
| 3'-Chlorobiphenyl-4-carboxylic acid | MS 230.9 (M⁻) |
| 2',3'-Difluorobiphenyl-4-carboxylic acid | MS 264.9 (M⁻) |
| 4'-Chlorobiphenyl-4-carboxylic acid | MS 230.9 (M⁻) |

Method D

2',4',6'-Trimethylbiphenyl-4-carboxylic acid

Combine 1-iodo-2,4,6-trimetbylbenzene (2.966 g, 12.05 mmol), 4-carboxyphenylboronic acid (1.0 g, 6.026 mmol), Pd(OAc)₂ (0.0067 g, 0.005 mmol), tetrabutylammonium bromide (0.388 g, 1.2055 mmol), and potassium phosphate (2.557 g, 12.05 mmol). Purge the reaction vessel with argon and add anhydrous DMF (20 ml) to the reaction mixture. Beat the sealed reaction vessel to 120° C. with stirring until completion as determined by TLC. Cool reaction mixture to room temperature. Add methyl iodide (1.0 ml, 36.63 mmol) to reaction mixture with continued stirring until completion. Dilute the reaction with ethyl acetate and filter though a short plug of celite with additional ethyl acetate. Wash the organics with water, dry over MgSO₄, filter and evaporate. Purification by flash column chromatography yields 2',4',6'-trimethylbiphenyl-4-carboxylic acid methyl ester as a yellow solid. Dissolve the purified ester in dioxane (45 ml) and water (5 ml) containing 5 eq of LiOH with stirring at 60° C. Upon completion, evaporate the solvent, acidify the reaction mixture with hydrochloric acid, and extract with ethyl acetate. Dry the organics over MgSO₄, filter, and evaporate to yield 0.023 g (16%) of the title compound. MS (m/e): 239.1 (M⁻).

The following compounds are prepared essentially as described above.

| | |
|---|---|
| 2',4',6'-Trifluorobiphenyl-4-carboxylic acid | MS 251.0 (M⁻) |
| 2'-Fluoro-4'-Trifluoromethylbiphenyl-4-carboxylic acid | MS 283.0 (M⁻) |

Method E

2',4'-Difluorobinhenyl-4-carboxylic acid

Combine 4-carbomethoxyphenylboronic acid (1.021 g, 5.67 mmol), 1-bromo-2,4-difluorobenzene (1.000 g, 5.181 mmol.), Pd(OAc)₂ (0.113 g, 0.50 mmol), triphenylphosphine (0.149 g, 0.505 mmol), and sodium carbonate (1.664 g, 0.568 mmol). Purge the reaction vessel with argon. Add DMF (20 mL) and water (2.0 mL) with stirring. Place sealed reaction in an 80° C. oil bath and allow to stir for 24 hours. Cool reaction to room temperature, dilute with ethyl acetate, and filter through a short plug of celite with additional ethyl acetate. Wash organics with water, dry over MgSO₄, filter, and evaporate. Purification by flash column chromatography yields 2',4'-difluorobiphenyl-4-carboxylic acid methyl ester as a yellow solid. Dissolve the purified ester in dioxane (5 ml) and add 5M NaOH (1 ml). Stir vigorously at 50° C. for 15 hours. Upon completion, acidify the reaction with conc. HCl and extract with ethyl acetate. Evaporation of the solvent yields 300 mg (24.7%) of the title compound. MS (m/e): 233.0 (M⁻).

Method F 6-(2,6-Difluorophenyl)pyridine-3-carboxylic acid

Dissolve 6-chloropyridine-3-carboxylic acid methyl ester (6.86 g, 40 mmol) in toluene (100 mL) and heat to 90° C. Add phosphorous oxybromide (25 g, 87 mmol) in several portions and continue heating for 3 hours. Cool the reaction to room temperature and pour onto ice water. Extract the reaction with ethyl acetate and wash organics again with water then NaHCO₃. Combine organics, dry over MgSO₄, filter, and evaporate to orange solid (8.1 g, 94%) which is an 8:1 mixture of 6-bromopyridine-3-carboxylic acid methyl ester:6-chloromopyridine-3-carboxylic acid methyl ester by ¹H NMR.

Combine the mixture as obtained above (0.225 g, 1.04 mmol) with hexamethylditin (0.375 g, 1.15 mmol), Pd(OAc)₂ (21 mg, 0.09 mmol), and triphenylphosphine (25 mg, 0.09 mmol) in toluene (5 mL). Purge with N₂ and stir at 80° C. for 18 hours. Cool reaction to room temperature. Add a solution of 1-bromo-2,6-difluorobenzene (250 mg, 1.29 mmol) in toluene (1 mL) followed by Pd(OAc)₂ (21 mg, 0.09 mmol) and triphenylphosphine (25 mg, 0.09 mmol). Purge with N₂ and stir at 80° C. for an additional 18 hours. Cool reaction to room temperature. Evaporate the solvent and purify by column chromatography (silica, 10% ethyl acetate in hexane) to give 50 mg (20% yield) of 6-(2,6-difluorophenyl)pyridine-3-carboxylic acid ethyl ester. Hydrolyze the ester with 1 N sodium hydroxide solution (0.22 mL, 0.22 mmol) in methanol (3 mL) at room temperature for 3 days. Remove the volatiles under vacuum and combine the residue with 1 N hydrochloric acid solution. Collect the white solid by filtration, wash with water, and dry under vacuum to give 30 mg (63% yield) of the title compound. MS (m/e): 235.9 (MH⁺).

Method G

3-Fluorobiphenyl-4-carboxylic acid

Combine methyl 2-fluoro-4-bromobenzoate (1.25 g, 5.36 mmol), phenylboronic acid (1.30 g, 10.72 mmol) and CsF (2.02 g, 13.40 mmol) in DMF (25 mL) and water (3.0 mL) with stirring. Place the hetereogeneous reaction mixture open to the air in an oil bath maintained at 80° C. After 5 minutes of heating, add Pd(OAc)₂ (120 mg, 0.536 mmol) in one portion and stir until reaction turns black. Cool reaction to room temperature, dilute with ethyl acetate and filter through a short plug of celite with additional ethyl acetate. Wash organics with water, dry over MgSO₄, filter and evaporate. Purification by flash column chromatography yields 3-fluorobiphenyl-4-carboxylic acid methyl ester as a solid. Dissolve the purified ester in THF (0.25M) and add an equal volume of 1 M NaOH. Stir vigorously at room temperature for 15 hours. Upon completion, acidify the reaction with conc. HCl and extract with ethyl acetate. Evaporation of the solvent yields 965 mg (84%) of the title compound. MS (m/e): 214.9 (M⁻).

The following compounds are prepared essentially as described above.

| | |
|---|---|
| 3-Fluoro-2'-methylbiphenyl-4-carboxylic acid | MS 229.0 (M⁻) |
| 2'-Chloro-3-fluorobiphenyl-4-carboxylic acid | MS 205.1 (M⁻) |
| 3-Fluoro-2'-trifluoromethylbiphenyl-4-carboxylic acid | MS 283.1 (M⁻) |

Method H

2-Fluoro-6-phenylpyridine-3-carboxylic acid

Dissolve 2,6-difluoropyridine (5.0 mL, 5.51 mmol) in anhydrous THF (30 mL) and cool to −40° C. Add a solution of phenyl lithium (1.8 M hexanes, 30.6 mL) dropwise over 5 minutes. Stir the resulting purple reaction at −40° C. for 30 minutes and bring to room temperature. Quench the reaction with water and extract the solution with ethyl acetate several times. Combine the organic extracts, dry over MgSO₄, filter and evaporate onto silica gel. Purification by flash column chromatography yields 2-fluoro-6-phenylpyridine 1.0 g (12%) as a yellow oil.

Cool a solution of LDA (3.46 mmol) in anhydrous THF (6 mL) to −78° C. Cannulate the 2-fluoro-6-phenylpyridine in anhydrous THF (6 mL) to the cooled LDA solution. Stir at −78 (C for 30 minutes then bubble carbon dioxide gas through the solution for 10 minutes. Allow the reaction to come to room temperature and purge with argon. Extract the reaction with 1 M NaOH and discard the organics. Acidify the aqueous layer with conc. HCl and extract with ethyl acetate. Dry the organic layer over MgSO₄, filter and evaporate to yield the title compound as a light yellow solid (405 mg, 65%). MS (m/e): 216.1 (M⁻).

Method J 3,5-Difluorobiphenyl-4-carboxylic acid

Combine 1-bromo-3,5-difluorobenzene (0.863 mL, 7.50 mmol) and phenylboronic acid (1.22 g, 10.00 mmol) and subject to conditions described in Method G to yield 1.3 g of 3,5-difluorobiphenyl.

Dissolve crude 3,5-difluorbiphenyl (1.3 g, 6.83 mmol) in THF (14 mL) and cool to. −78° C. Prepare LiTMP from the addition of BuLi (1.6 M soln in hexanes, 5.33 mL) to tetramethyl piperidine (1.4 mL, 1.25 equiv) at −78° C. in THF (14 mL). Cannulate the cooled LiTMP into the cooled 3,5-difluorobiphenyl and stir the reaction at −78° C. for 1 h. Bubble carbon dioxide gas through the solution for 5 minutes, warm the reaction to rt, pour into 50 mL of 1M NaOB, and extract with 50 mL EtOAc. Discard the organic layer was discarded. Acidify the remaining aqueous layer with conc. HCl and extract twice with EtOAc. Dry the organics over MgSO₄, filtered, and evaporate to give 1.22 g of the title compound as a white solid (77%). MS (m/e): 233.1 (M⁻).

Method K 3,2',6'-Trifluorobiphenyl-4-carboxylic acid

Combine methyl 4-bromo-2-fluorobenzoate (3.66 g, 15.75 mmol), 4,4,5,5,4',4',5',5'-octamethyl-2,2'-bi-1,3,2-dioxaborolanyl (5.0 g, 19.68 mmol) and potassium acetate (4.63 g, 47.19 mmol) in DMSO (40 mL) and purge the solution with argon. Add PdCl₂(1,1'-bis(diphenylphosphino) ferrocene)₂ (10 mol %, 1.35 g) and purge the solution with argon again. Heat the reaction to 80° C. for 3 h and cool to room temperature. Wash the reaction with water and extract with ethyl acetate and concentrate. The resulting black oil is re-dissolved in 1:2 ethyl acetate:hexanes, filtered through a short plug of silica gel, and concentrated. 2-Fluoro-4-(4,4,5,5-tetramethyl-1,3,2-dioxaborolan-2-yl)benzoic acid methyl ester is obtained as a yellow oil.

Dissolve the resulting yellow oil in acetone (100 mL) and combine with NaIO₄ (10.1 g, 47.25 mmol), NH₄OAc (3.63 g, 47.25 mmol), and water (50 mL) at room temperature. Stir at room temperature for 18 h, transfer to a separatory funnel and extract with ethyl acetate several times. Dry the combined organics over MgSO₄, filter and concentrate to yield 3.0 g of 3-fluoro-4-carbomethoxybenzene boronic acid as an off-white solid.

The boronic acid obtained above (800 mg, 4.04 mmol) and 2,6-difluorobromobenzene (1.17 g, 6.06 mmol) are coupled according to the procedure described in Method G to give 380 mg of the title compound. MS (m/e): 251.1 (M⁻¹).

Method L

6-Phenylpyridazine-3-carboxylic acid

6-Phenylpyridazin-3-ol (5.0 g, 29.06 mmol) is dissolved in toluene (100 mL) and heated to 900° C. Phosphorous oxybromide (25 g, 87.19 mmol) is added in several portions and the reaction is heated for 30 minutes. The resulting yellow solution is cooled to room temperature, poured onto ice water, and extracted with ethyl acetate. The organic layers are further washed with water and 1M NaOH, dried over MgSO₄, filtered, and evaporated to a yellow solid. Recrystallization from CHCl₃ gives 2.17 g of 3-bromo-6-phenylpyridazine.

3-Bromo-6-phenylpyridazine (1.0 g, 4.25 mmol) is combined with DMF (5 mL), MeOH (5 mL), triethylamine (1.18 mL, 8.50 mmol), and Pd(OAc)₂ (76 mg, 0.33 mmol) and the mixture evacuated. 1,1'-Bis(diphenylphosphino)ferrocene (235 mg, 0.42 mmol) is added and the reaction is again evacuated. Carbon dioxide gas is bubbled through the solution for 5 minutes, and the reaction is placed under 50 psi (345 kPa) of carbon dioxide. The resulting solution is heated at 50° C. for 18 h. The reaction is cooled to room temperature, diluted with water, and extracted with ethyl acetate. The organics are dried over MgSO₄, filtered, and evaporated onto silica gel and subjected to flash column chromatography.

Hydrolysis using conditions outlined in Method A gives 80 mg of the title compound. ¹H NMR (CDCl₃): 8.24 (d, 1H, J=8.8 Hz), 8.18-8.15 (m, 2H), 8.0 (d, 1H, J=9.2 Hz), 7.56-7.55 (m, 3H).

Method M 6-(4-Fluorophenyl)pyridine-3-carboxylic acid

Combine 6-bromopyridine-3-carboxylic acid methyl ester (1.03 g, 4.78 mmol), 4-fluorophenylboronic acid (1.88 g, 13.41 mmol), and cesium fluoride (2.55 g, 16.78 mmol) in DMF (25 mL) and water (4 mL) with stirring. Place the hetereogeneous reaction mixture, open to the air, in an oil bath maintained at 80° C. After 5 minutes of heating, add Pd(OAc)₂ (150 mg, 0.67 mmol) in one portion. After 17 hours, cool the reaction to room temperature, dilute with ethyl acetate and filter through a short plug of celite with additional ethyl acetate. Wash the organics with water, dry over MgSO₄, filter and evaporate. Purification by flash column chromatography yields 6-(4-fluorophenyl)pyridine-3-carboxylic acid methyl ester as a yellow solid. Dissolve the purified ester in THF (0.25M) and add an equal volume of 1M NaOH. Stir vigorously at room temperature for 15 hours. Upon completion, acidify the reaction with conc. HCL and collect the white precipitate by filtration. Drying under vacuum yields 385 mg (37%) of the title compound. MS (m/e): 218.1 (MH$^+$)

The following compound is prepared essentially as described above.

| | |
|---|---|
| 6-(Thien-2-yl)pyridine-3-carboxylic acid | MS 205.9 (MH$^+$) |

Method N 6-(4-Fluoro-2-methylphenyl)pyridine-3-carboxylic acid

Combine 6-bromopyridine-3-carboxylic acid methyl ester (387 mg, 1.79 mmol), 4-fluoro-2-methylphenylboronic acid (338 mg, 2.19 mmol), Pd(OAc)₂ (40 mg, 0.18 mmol), cesium fluoride (27 mg, 0.18 mmol) and sodium carbonate (570 mg, 5.38 mmol) in DMF (6 mL) and water (6 mL) with stirring. Purge the reaction mixture with N₂, add triphenylphosphine (47 mg, 0.18 mmol), and purge again with N₂. Place the sealed reaction in an oil bath maintained at 80° C. and allow to stir for 17 hours. Cool the reaction to room temperature and pass through a short plug of silica gel. Wash the column with dichloromethane (100 mL) followed by aqueous methanol (100 mL, 3 methanol/1 water). Reduce the combined fractions in vacuo and suspend the residual solid in water (10 mL). Filter to remove a black solid and acidify with 1 N hydrochloric acid solution to pH 4. A white precipitate forms which is collected by filtration and dried to give 306 mg (74%) of the title compound. MS (m/e): 231.9 (MH$^+$).

The following compounds are prepared essentially as described above.

| | |
|---|---|
| 6-(2,4-Difluorophenyl)pyridine-3-carboxylic acid | MS 236.0 (MH$^+$) |
| 6-(2-Fluorophenyl)pyridine-3-carboxylic acid | MS 218.0 (MH$^+$) |
| 2'-Fluorobiphenyl-4-carboxylic acid | MS 215.1 (M$^-$) |
| 2'-Methylbiphenyl-4-carboxylic acid | MS 211.2 (M$^-$) |

EXAMPLE 1-1

Biphenyl-4-carboxylic acid (R)-(6-(1-((4-fluorobenzyl)methylamino)ethylideneamino)-2(R)-hydroxyindan-1-yl)amide

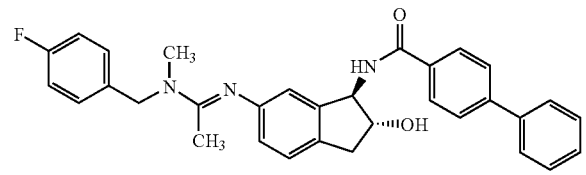

Slowly add a solution of 375 g (5.13 mol, 1.12 equiv) of N-methylacetamide in THF (1.76 L) to 224 g (5.55 mol, 1.2 equiv) of sodium hydride (60% dispersion in mineral oil) as a slurry in THF (8.75 L). After 30 minutes when 25% of the solution has been added, add 875 g (4.63 mole, 1 equiv) of 4-fluorobenzylbromide and the remaining N-methylacetamide and 4-fluorobenzylbromide solutions concurrently over the next 3 h. Use a water bath to maintain the temperature below 40° C. Stir the resulting mixture overnight and pour into a mixture of 20% NH₄Cl (2.5 L), water (6.5 L), and ethyl acetate (9 L). Separate the layers and back-extract the aqueous layer with ethyl acetate (4.5 L, then 2 L). Combine the organic layers and wash with water (4 L) and then brine (7 L). Dry the organic layer (Na₂SO₄) and remove the solvent to afford a residue. Dissolve the residue in acetonitrile (7 L) and heptane (1.75 L). Separate the layers and wash the acetonitrile layer again with heptane (1.75 L). Combine the heptane layers and back-extract with acetonitrile (0.5 L). Combine the acetonitrile layers and evaporate to afford 0.814 kg of N-methyl-N-(4-fluorobenzyl)acetamide.

Dissolve N-methyl-N-(4-fluorobenzyl)acetamide (0.500 kg, 2.76 mol) in THF (11.5 L). Add phosphorus pentasulfide (0.737 kg, 1.65 mol, 0.6 equiv) and heat the mixture to reflux over 1-2 hours. After 5 h at reflux, allow the mixture to cool to room temperature, filter off the solids, and wash with 12.5 L of THF. Combine the filtrate with an identical filtrate from a separate reaction and concentrate to 0.978 kg of a residue. Dissolve the residue and chromatograph on 2.7 kg of silica gel using CH₂Cl₂ to afford 1.01 kg of solid. Slurry the solid with methylene chloride (1 L) for 15-30 min, add heptane (5 L), cool the mixture to 0-5° C., and stir for 2 h. Collect the solid by filtration and dry to afford 0.814 kg of N-methyl-N-(4-fluorobenzyl)thioacetamide.

Add 11.5 L of acetonitrile and 2.52 kg (17.7 mol, 1.5 equiv) of methyl iodide to 2.30 kg (11.6 mol) of N-methyl-N-(4-fluorobenzyl)acetamide. Heat the mixture to 35° C. for 21 h. Reduce the volume by half on a rotary evaporator and add 14 L of MTBE. Reduce the volume again by half and add another 14 L of MTBE. Cool the resulting slurry to 0° C., collect the solid by filtration, and dry to afford 3.92 kg of 1-methylthio-1-methyl-N-(4-fluorobenzyl)-N-methylimmonium iodide as a white solid.

Add 85 L of concentrated NH₄OH and 28 L of water to 6.20 kg (35.0 mol) of 1,2-epoxy-6-nitroindane. Heat the mixture at 36° C. for 21 h and allow to cool to room temperature. Filter the reaction mixture over a bed of wet Celite (10 kg) and rinse the cake with water. Add to the wet cake 155 L of methanol, 1.3 L of water, and 5.80 kg (38.1 mol, 1.09 equiv) of (S)-(+)-mandelic acid. Heat the mixture for 2 h at 55° C. and filter through a carbon impregnated filter cartridge. Reduce the filtrate volume by vacuum distillation to about 35 L and add 130 L of EtOAc. Reduce the volume by vacuum distillation to about 65 L. Cool the mixture to −8° C. and stir for 8 h. Filter the slurry and dry the solid to afford 7.6 kg of a solid. Slurry this solid in 30 L of methanol and 0.3 L of water, and heat the mixture at reflux for 0.5 h. Cool the mixture to 45° C. over 0.5 h and stir for 12 h, followed by cooling to 22° C. and stirring for 10 h. Collect the solid by filtration and dry to afford 2.7 kg of 1(R)-amino-2(R)-hydroxy-6-nitroindane (S)-mandelate.

Add 1(R)-amino-2(R)-hydroxy-6-nitroindane (S)-mandelate (0.64 kg, 1.85 mol) to a mixture of toluene (9.6 L) and aqueous 1 N NaOH (4.8 L, 4.8 mol, 2.6 equiv). After 1 h, add 4-biphenylcarbonyl chloride (0.44 kg, 2.0 mol, 1.1 equiv) in portions over 20-30 min. After 22 hours, filter the solids under vacuum and rinse sequentially with 0.5 L of toluene, 2 L of water, and 2 L of toluene. Dry the cake to afford 0.74 kg of biphenyl-4-carboxylic acid (R)-(6-nitro-2-hydroxyindan-1-yl)amide. Add 38.2 L of ethyl acetate to 1.914 kg of biphenyl-4-carboxylic acid (R)-(6-nitro-2(R)-hydroxyindan-1-yl)amide prepared in a similar manner. Stir the slurry for 18 h, collect the solid by filtration, dry to afford 1.76 kg of biphenyl-4-carboxylic acid (R)-(6-nitro-2(R)-hydroxyindan-1-yl)amide as a white solid.

Combine a slurry of 0.176 kg of 10% Pd-C (50% water wet) and 1.7 kg of biphenyl-4-carboxylic acid (R)-(6-nitro-2(R)-hydroxyindan-1-yl)amide in 17.5 L of DMF with hydrogen (50 psi, 345 kPa). After 19 h, filter the reaction mixture, add a portion of the DMF solution (5 L) to water (10 L), and stir the slurry for 2 h-repeat twice to work up the entire reaction volume. Filter the slurries together, and wash the resulting filter cake with water (3×7 L). Dry the filter cake to afford 1.42 kg of biphenyl-4-carboxylic acid (R)-(6-amino-2(R)-hydroxyindan-1-yl)amide.

Slurry biphenyl-4-carboxylic acid (R)-(6-amino-2(R)-hydroxyindan-1-yl)amide (0.969 kg, 2.81 mol) in THF (9.7 L) and add 1-methylthio-1-methyl-N-(4-fluorobenzyl)-N-methylimmonium iodide (0.954 kg, 2.81 mol) and 4-dimethylaminopyridine (34.5 g, 0.281). Stir the mixture for 24 h, and remove the solvent in vacuo. Dissolve the resulting foam in $CH_2Cl_2$ (12.5 L) and wash the organic phase with 1.0 N HCl (1×4 L and 1×3 L), 1.0 M NaOH (1×2.4 L) and saturated NaCl (1×4 L). Separate the organic phase, dry ($Na_2SO_4$), filter, and remove the solvent to yield a solid. Dissolve the solid in acetonitrile (9 L) while heating to 35-40° C. After approximately 30 minutes, add seed crystals, which results in a thick, white slurry. Cool the mixture to −15° C. and stir at this temperature for 1-2 h. Filter the slurry and dry to provide 1.10 kg of the title compound as a partial acetonitrile solvate.

$^1$H NMR (CDCl$_3$): δ 7.90 (d, 2, J=8.6), 7.69 (d, 2, J=8.6), 7.63 (d, 2, J=8.2), 7.48 (t, 2, J=8.2, 7.6), 7.41 (d, 1, J=7.3), 7.24 (dd, 2, J=8.5, 5.2), 7.14 (d, 1, J=7.9), 7.04 (t, 2, J=8.7), 6.72-6.63 (m, 3), 5.31 (t, 1, J=5.6), 4.84 (br s, 1), 4.64 (dd, 2, J=21.4, 15.6), 4.54 (dd, 1, J=14.0, 7.9), 3.32 (dd, 1, J=15.6, 7.9), 3.01 (s, 3), 2.95 (dd, 1, J =15.7, 8.0), 1.97 (s, 3). MS (m/z): 508.2 (M+1).

EXAMPLE 2-1

Biphenyl-4-carboxylic acid (R)-(6-(1-((4-fluorobenzyl)methylamino)ethylideneamino)-2(R)-hydroxyindan-1-yl)amide

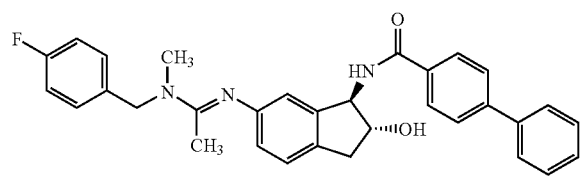

Combine trans-1-amino-2-hydroxy-6-nitroindane (20.2 g, 0.10 mol) and S-mandelic acid (16.7 g, 0.11 mol, 1.1 equiv) in 173 mL of methanol and 3.6 mL of water. Heat at reflux and then add 200 mL of ethyl acetate. Seed and allow to cool to 23° C. After stirring for 4 h at 23° C., cool for 3 hr at −3° C., then filter and rinse with cold 40% methanol and 60% ethyl acetate to give a solid. Dry the solid in a vacuum oven at 45° C. for 16 h to afford a 59:41 mixture of diastereomeric salts favoring 1(R)-amino-2(R)-hydroxy-6-nitroindane.

Combine the 59:41 mixture of diastereomeric salts with 35 mL of methanol and 0.32 g of water. Heat to about 64° C., allow to cool to about 45° C., and stir for 14 h and then at 23° C. for 14 h to give a solid. Collect the solid by filtration, rinse with methanol, and dry in a vacuum oven at 45° C. for 26 h to afford 2.64 g of 1 (R)-amino-2(R)-hydroxy-6-nitroindane S-mandelate of high enantiomeric purity. HRMS (m/z): 194.0691. IR (CHCl$_3$) 1347, 1074 cm$^{-1}$.

Combine 1(R)-amino-2(R)-hydroxy-6-nitroindane S-mandelate 40.2 g (116.1 mmol), 320 mL of water, 650 mL of ethyl acetate, 26.6 g of di-tert-butyldicarbonate (121.9 mmol, 1.05 equiv), and an additional 200 mL of ethyl acetate. Add 120 mL of 1 N aqueous sodium hydroxide (120 mmol, 1.03 equiv) dropwise. After 15 h, a solid forms.

Collect the solid and rinsed with water (3 times) and ethyl acetate (3 times). Dry to give 1(R)-(t-butoxycarbonylamino)-2(R)-hydroxy-6-nitroindane as white solid 19.4 g (57%): MS (m/z): 295 (M+1). [α]D=−111 (c=1, MeOH).

Combine 1 (R)-(t-buloxycarbonylamino)-2(R)-hydroxy-6-nitroindane 30.5 g (0.11 mol), 800 mL of THF, 800 mL of ethyl acetate and 6.3 g of 5% palladium on carbon. Hydrogenate at 50 psi (345 kPa) of hydrogen for 2 h. Remove the catalyst by filtration and evaporate the solvent to give 29.5 g 1(R)-(t-butoxycarbonylamino)-2(R)-hydroxy-6-aminoindane: MS (m/z): 265 (M+1). IR (KBr) 1699, 1625, 1535 cm$^{-1}$. [α]D=−122 (c=1, MeOH).

To a solution of NaH (6.86 g, 0.172 mole, 60% in mineral oil, 1.3 equiv) in THF (250 mL), add dropwise a solution of N-methylacetamide (11.6 g, 0.159 mole, 1.2 equiv) in THF (90 mL). After about 20 min, add 4-fluorobenzylbromide (25 g, 0.132 mole). Stir for about 62 hours then pour over ice water (300 mL) and extract with ethyl acetate (400 mL and 200 mL). Combine the organic layers and wash with water (300 mL), dry over Na$_2$SO$_4$, filter and concentrate to an oil. Dissolve the oil in acetonitrile and extract with hexane to remove the mineral oil to give 22.79 g N-methyl-N-(4-fluorobenzyl)acetamide: mp=48-54° C.; R$_f$=0.45 (4% MeOH/methylene chloride); $^1$H NMR (CDCl$_3$) 7.27-6.93 (m, 4), 4.5 (d, 2), 2.91 (s, 3), 2.14 (s, 3).

Combine N-methyl-N-(4-fluorobenzyl)acetamide (364.8 g, 2.01 mol) and THF (9 L). Stir to afford a solution, then add phosphorus pentasulfide (537.7 g, 1.21 mol). After 45 min, heat to reflux. After 3 h, allow to cool and stir overnight to give a solid. Remove the solid by filtration and rinse the filter cake with THF (4 L). Evaporate the filtrate to give a residue, dissolve in methylene chloride (500 mL) and passed over a short column of silica gel 60 (1.2 kg) preconditioned with heptane. Elute with 4 L of heptane/methylene chloride (1:1) followed by 100% methylene chloride to afford, after collection and drying, 217.98 g of N-methyl-N-(4-fluorobenzyl)thioacetamide: mp=99-104° C.; Rf=0.42 (methylene chloride); $^1$H NMR (CDCl$_3$) 7.35-7.26 (m, 1), 7.14-6.96 (m, 3), 5.28 (s, 1.2) and 4.79 (s, 0.8), 3.42 (s, 1.2) and 3.15 (s, 1.8), 2.72 (s, 1.2) and 2.69 (s, 1.8). Note: Partial protons are believed to be due to rotomers.

Combine N-methyl-N-(4-fluorobenzyl)thioacetamide (14.03 g, 0.0711 mole) and methylene chloride (140 mL) under nitrogen and cool in an ice water bath. Add dropwise methyl trifloromethanesulfonate (9.66 mL, 0.085 mole, 1.2 equiv). After 15 min, remove the ice bath and stir for 2 hr. Remove the solvent under vacuum to obtain 25.89 g (100%) of 1-methylthio-1-methyl-N-(4-fluorobenzyl)-N-methylimmonium triflate.

Combine 1-methylthio-1-methyl-N-(4-fluorobenzyl)-N-methylimmonium triflate (5 g, 13.8 mmol), methylene chloride (50 mL) and 1(R)-(t-butoxycarbonylamino)-2(R)-hydroxy-6-aminoindane (3.65 g, 13.8 mmol) under nitrogen. Add pyridine (0.15 mL). After 2.5 hr a solid was formed. Collect the solid was by filtration, rinse with a minimal amount of methylene chloride, and dry in a vacuum oven to give 6.29 g (79%) of 1(R)-(t-butoxycarbonylamino)-2(R)-hydroxy-6-(1-methyl-N'-(4-fluorobenzyl)-N'-methylamidino)indane triflate as a white solid. mp=123-132° C.

Cool trifluoroacetic acid (TFA, 66 mL) in an ice bath and add 1(R)-(t-butoxycarbonylamino)-2(R)-hydroxy-6-(1-methyl-N'-(4-fluorobenzyl)-N'-methylamidino)indane triflate (29.65 g, 0.051 mole) in portions along with 3 mL of methylene chloride. Stir in the ice bath for 10 min and then allow to warm room temperature and stir for 1.5 hr. Partition the reaction mixture between methylene chloride (500 mL) and ice water (500 mL). Add 2M aqueous sodium hydroxide (450 mL) and separate the layers. Extract the aqueous layer with methylene chloride (250 mL) and the combined organic layers were washed with water (300 mL). Cool the organic layer, add 1N aqueous sodium hydroxide (76 mL) and water (76 mL) and stir to give.

To the N'-(3-amino-2-hydroxyindan-5-yl)-N-(4-fluorobenzyl)-N-methylacetamidine produced by the above procedures, add 4-biphenylcarbonyl chloride (11.05 g, 0.051 mole, 1 equiv) in portions. Add an additional 50 mL of water. After 2 h, separate the layers, extract the organic layer with water (300 mL), dry over $Na_2SO_4$, filter and evaporate to give 27.06 g of the title compound as a white foam.

Crystallize a 10 g portion of the title compound from 10 mL/g of acetonitrile to afford 5.96 g of the title compound: mp 103-111° C. MS (m/z): 508 (M+1).

Slurry the title compound obtained by recrystallization above in a mixture of 45 mL of ethyl acetate and 45 mL of hexane for 16 h to afford the title compound mp 139-142° C.

Combine the title compound having mp 139-142° C. (1 g) and absolute ethanol (12 mL). Heat to about 50° C. until the solids dissolve. Add deionized water (4.5 mL) dropwise followed by the addition of seed crystals of the polymorph melting at about 150-152° C. Cool to about 23° C. over 1.5 h, to give a thick suspension. Cool the suspension in an ice bath, filter, and dry in a vacuum oven at 50-60° C. to yield 0.76 g of the title compound: mp 150-152° C.

As will be understood by one of ordinary skill in the art, an alternate name for the title compound is 6-(1-((4-fluorobenzyl)methylamino)ethylideneamino)-2-hydroxy-1-biphenylamidoindane.

EXAMPLE 2-2

Biphenyl-4-carboxylic acid (R)-(6-(1-((4-fluorobenzyl)methylamino)ethylideneamino)-2(R)-hydroxyindan-1-yl)-amide

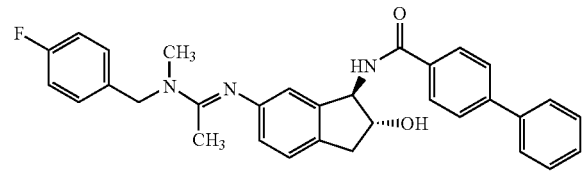

Combine 1(R)-amino-2(R)-hydroxy-6-nitroindane S-mandelate 50.0 g (0.144 mole) and 750 mL of toluene. Add 375 mL (0.375 mole, 2.6 equiv) of 1N aqueous sodium hydroxide followed by 470 mL of water. Stir for about 22 minutes then add 35.5 g (0.159 mole, 1.1 equiv) of 4-biphenylcarbonyl chloride portion-wise over about 6 minutes. After 3.5 h, filter the resulting slurry, rinse the filter cake with toluene, dry in vacuo at 50° C. for 18 h to give 56.1 g of 1(R)-(4-biphenylcarbonylamino)-2(R)-hydroxy-6-nitroindane: 1R (KBr, cm$^{-1}$): 3293, 1640, 1549, 1528, 1345, 1329, 1086, 739; HRMS calc'd for $C_{22}H_{18}N_2O_4$:374,1267, Found: 374,1266.

Combine 1 (R)-(4-biphenylcarbonylamino)-2(R)-hydroxy-6-nitroindane 55.7 g, 550 mL of DMF and 2.8 g of 10% Pd/C catalyst. Hydrogenate at 50 psi (345 kPa) of hydrogen at ambient temperature for 4.75 h. Filter the reaction mixture and dilute the filtrate with 1200 mL of water to give a slurry. Stir the slurry for 30 minutes, filter, wash with water, and dry in vacuo at 50° C. Combine the dried product and about 1 L of water and slurry for 30 minutes, filter, wash with water, and dry in vacuo at 50° C. to afford 45.4 g (90%) of 1 (R)-(4-biphenylcarbonylamino)-2(R)-hydroxy-6-aminoindane: 1R (KBr, cm$^{-1}$); 3584, 3364, 3277, 1632, 1543, 1326, 1073, 743; HRMS calc'd for $C_{22}H_{20}N_2O_2$: 344,4120; Found: 344,1525.

Combine N-methyl-N-(4-fluorobenzyl)acetamide (364.8 g, 2.01 mol) and THF (9 L). Stir to dissolve and then add phosphorus pentasulfide (537.7 g, 1.21 mol). After 45 min heat to reflux for 3 h, then cool and stir overnight to give a solid. Collect the solid by filtration and rinse the cake with THF (4 L), evaporate the filtrate in vacuo to give a residue, dissolve the residue in methylene chloride (about 500 mL), and passed over a cake of silica gel 60 (1.2 kg) preconditioned with heptane. Elute with 4 L of heptane/methylene chloride (1:1) followed by 100% methylene chloride to afford 217.98 g of N-methyl-N-(4-fluorobenzyl)thioacetamide (55%): mp=99-104° C.; Rf=0.42 (methylene chloride); $^1$H NMR (CDCl$_3$) 7.35-7.26 (m, 1), 7.14-6.96 (m, 3),5.28 (s, 1.2) and 4.79 (s, 0.8), 3.42 (s, 1.2) and 3.15 (s, 1.8), 2.72 (s, 1.2) and 2.69 (s, 1.8). Note: Partial protons are believed to be due to rotomers.

Add methyl iodide (10.76 g, 75.8 mmol) in one portion to a suspension of N-methyl-N-(4-fluorobenzyl)thioacetamide (10 g, 50.6 mmol) in acetonitrile (50 mL). Heat at 35° C. for 46 h, then cooled to about 23° C. Reduce the volume of the reaction mixture to about 25 mL by evaporation and then add methyl t-butyl ether (50 mL). Again reduce the volume by evaporation to 25 mL again and then dilute with another 50 mL of methyl t-butyl ether to give a solid. Cool to 0° C., filter, rinse with 15 mL of cold methyl t-butyl ether, and dry to yield 16.89 g of 1-methylthio-1-methyl-N-(4-fluorobenzyl)-N-methylimmonium iodide as a yellow solid, mp 142-150° C. MS (Electrospray): theoretical for iminium portion $C_{11}H_{15}FNS$: 212; Found: 212.

Combine 1(R)-(4-biphenylcarbonylamino)-2(R)-hydroxy-6-aminoindane 10.0 g (0.029 mol), 4-dimethylaminopyridine (DMAP) 0.4 g (0.0032 mol, 0.011 equiv), 200 mL of acetone and 1-methylthio-1-methyl-N-(4-fluorobenzyl)-N-methylimmonium iodide 10.8 g (96% potency, 0.0305 mol, 1.05 equiv). After 6 h, concentrate the reaction mixture to a foam. Combine the foam and 120 mL of toluene, stir at ambient temperature for 19.5 h, filter, dry in vacuo at 50° C. to give a residue, the hydroiodide salt of the title compound, characterized by the following NMR: $^1$H NMR (CDCl$_3$,300 MHz): δ 8.02 (d, J=9.0 Hz, 2H); 7.82-7.93 (m,1H); 6.90-7.69 (m, 14H); 4.85-5.25 (m, 2H); 4.60-4.80 (m, 2H); 3.45 (s, 2H); 3.00-3.20 (m, 2H); 2.60-2.75 (m, 1H); 2.10-2.35 (m, 4H).

Dissolve the residue in 200 mL of methylene chloride and extract with 200 mL of 1.0 M aqueous sodium hydroxide followed by 200 mL of brine. Dry the organic layer over MgSO$_4$, filter, and evaporate in vacuo to afford 15 g of the title compound.

Combine 5.0 g of the compound obtained above and 200 mL of methylene chloride. Add 1.00 g of DARCO carbon, stir for 1 h, and then filter through a bed of Hyflo. Evaporate in vacuo to afford 4.0 g of a residue. Dissolve the residue in absolute ethanol (about 40 mL) and add deionized water (12 mL) to give a solid. Heat the slurried solid to 55° C. for 30 min, allow to cool to room temperature, and stirred. After 24 h, filter, rinse with 10 mL of a 10:3 EtOH:water mixture, dry in vacuo to afford 1.5 g of the title compound: mp 108-112° C.

One of ordinary skill in the art will recognize that an alternate name for the title compound is 6-(1-((4-fluorobenzyl)methylamino)ethylideneamino)-2-hydroxy-1-biphenylamidoindane.

EXAMPLE 3-1

3-Fluorobiphenyl-4-carboxylic acid (R)-(6-(1-((4-fluorobenzyl)methylamino)ethylideneamino)-2(R)-hydroxyindan-1-yl)amide

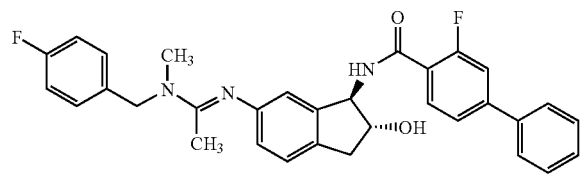

Combine 4-bromo-2-fluorobenzoic acid (10 g, 45.7 mmol), methanol (100 mL), and concentrated sulfuric acid (5.0 mL). Heat to reflux. After 16 h, cool to room temperature and evaporate in vacuo to afford a white solid. Dissolve the solid in ethyl acetate (about 40 mL), extract with 2×80 mL saturated aqueous sodium bicarbonate and 1×80 mL brine, dry over MgSO$_4$, filter, and evaporate in vacuo to yield 9.32 g (88%) of methyl 4-bromo-2-fluorobenzoate as a white solid. $^1$H NMR (d$_6$-DMSO, 300 MHz) 8.80 (t, J=8.4 Hz, 1H), 7.72 (dd, J=10.8 Hz, 1.8 Hz, 1H), 7.54 (ddd, J=8.4 Hz, 1.8 Hz, 0.6 Hz, 1H), 3.83 (s, 3H); IR (cm$^{-1}$, KBr): 3010, 2995, 1723, 1603, 1484, 1438, 1406, 1294, 1277, 1095, 885; Anal calc'd for C$_8$H$_6$BrFO$_2$: C, 41.23; H, 2.60; Found: C, 40.97; H, 2.61.

Combine methyl 4-bromo-2-fluorobenzoate (9.3 g, 40.0 mmol), phenylboronic acid (9.75 g, 80.0 mmol), and cesium fluoride (32.6 g, 100.1 mmol), DMF (190 mL) and deionized water (50 mL). Heat to 80° C. and add Pd(OAc)$_2$ (303 g, 4.0 mmol). After 20 min, cool to room temperature, filter through HyFlo with the aid of 100 mL ethyl acetate, extract the filtrate with 2×100 mL 5% aqueous lithium chloride, 2×50 mL 1.0 M aqueous sodium hydroxide, and 2×100 mL brine. Separate the organic phase, dry over MgSO$_4$, filter, and evaporate in vacuo to yield 8.85 g (96%) of methyl 3-fluorobiphenyl-4-carboxylate as a white solid. $^1$H NMR (CDCl$_3$, 300 MHz) 8.01 (t, J=7.8 Hz, 1H), 7.58-7.62 (m, 2H), 7.41-7.51 (m, 4H), 7.37 (m, 1H), 3.96 (s, 3H); IR (cm$^{-1}$, KBr): 3033, 2954, 1721, 1622, 1437, 1409, 1298, 1289, 1266, 1097; Anal calc'd for C$_{14}$H$_{11}$FO$_2$: C 73.03, H 4.82; Found: C 73.06, H 4.86.

Combine methyl 3-fluorobiphenyl-4-carboxylate (8.18 g, 35.5 mmol), THF (225 mL), and 1.0 M aqueous sodium hydroxide (225 mL). Heat at 50° C. for 8 h. Cool to room temperature, add 1.0 M aqueous hydrochloric acid (300 mL), and extract with 2×200 mL ethyl acetate. Separate the organic phase, dry over MgSO$_4$, filter, and evaporate in vacuo to afford 7.12 g (93%) of 3-fluorobiphenyl-4-carboxylic acid as a white solid. $^1$H NMR (d$_6$-DMSO, 300 MHz) 13.22 (br s, 1H), 7.93 (t, J=8.1 Hz, 1H), 7.74-7.78 (m, 2H), 7.60-7.66 (m, 2H), 7.40-7.52 (m, 3H); IR (cm$^{-1}$, KBr): 3035, 2666, 2575, 1699, 1621, 1563, 1408, 1298, 1265, 1193, 904; Anal calc'd for C$_{13}$H$_9$FO$_2$: C 72.22, H 4.20; Found: C 72.18, H 4.35.

Combine 3-fluorobiphenyl-4-carboxylic acid 10.46 g (0.048 mol), 432 mL of methylene chloride, 7 drops of dimethylformamide, and 5.44 mL (0.062 mol, 1.3 equiv) of oxalyl chloride. After 2 h, evaporate the solvent to afford 3-fluorobiphenyl-4-carbonyl chloride as a solid.

Combine 1-methylthio-1-methyl-N-(4-fluorobenzyl)-N-methylimmonium triflate 20.96 g (0.58 mol), 53 mL of pyridine, and 1(R)-(t-butoxycarbonylamino)-2(R)-hydroxy-6-aminoindane 15.33 g (0.58 mol, 1 equiv). After 4.2 h, evaporate by rotary evaporation to remove most of the pyridine, add ethyl acetate, and remove by rotary evaporation to give a residue. Store the residue overnight at 0° C., add ethyl acetate (400 mL), and extract with 200 mL of 1 N aqueous sodium hydroxide followed by 200 mL of water. Dry the organic layer over Na$_2$SO$_4$, filter and evaporate to give a residue. Chromatograph the residue on silica gel eluting with a gradient of 3-10% methanol in methylene chloride to afford 18.85 g (76%) of 1 (R)-(t-butoxycarbonylamino)-2(R)-hydroxy-6-(1-methyl-N'-(4-fluorobenzyl)-N'-methylamidino)indane: MS m/z=428 (M+1), mp=123-132° C.

Combine 1 (R)-(t-butoxycarbonylamino)-2(R)-hydroxy-6-(1-methyl-N'-(4-fluorobenzyl)-N'-methylamidino)indane 18.86 g (0.044 mol) and 110 mL of trifluoroacetic acid in an ice bath. When the addition is complete remove the ice bath and stir at room temperature for 2.5 h. Evaporate the reaction mixture by rotary evaporation to afford a residue. Dissolve the residue in 100 mL of methylene chloride and cool in an ice bath to about 13° C., add 1N aqueous sodium hydroxide (272 mL), followed by 3-fluorobiphenyl-4-carbonyl chloride 11.26 g (0.048 mol, 1.1 equiv) dissolved in 120 mL of methylene chloride. Add an additional 30 mL of 1 N aqueous sodium hydroxide and stir at about 10° C. for 40 min. Partition the reaction mixture between water and methylene chloride. Separate the layers and extract the organic with water, dry, and concentrated on a rotary evaporator to afford 20.67 g of residue. Chromatograph the residue on silica gel eluting with a gradient of 3-10% methanol in methylene chloride, followed by a second chromatography on silica gel using a Prep 2000 eluting with a gradient of 3-10% methanol in methylene chloride, to afford 11.34 g (49%) of the title compound: MS m/z=526 (M+1).

As will be understood by one of ordinary skill in the art, an alternate name for the title compound is 6-(1-((4-fluorobenzyl)methylamino)ethylideneamino)-2-hydroxy-1-(2-fluorobiphenylamido)indane.

EXAMPLE 4-1

2',6'-Dichlorobiphenyl-4-carboxylic acid (R)-(6-(1-((4-fluorobenzyl)methylamino)ethylideneamino)-2(R)-hydroxyindan-1-yl)amide

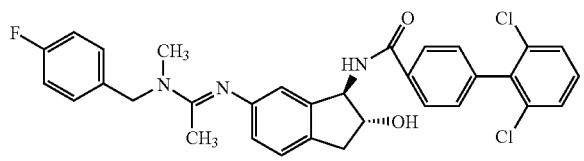

Add DMF (1.6 mL) to a mixture of N-cyclohexylcarbodiimide-N-methylpolystyrene resin (Novobiochem, 2.0 mmol/g) (150 mg, 0.30 mmol) and 2',6'-dichlorobiphenyl-4-carboxylic acid (14 mg, 0.05 mmol) followed by a solution of N-hydroxysuccinimide (2.3 mg, 0.02 mmol) in DMF (0.2 mL) and then a solution of N'-(3-amino-2-hydroxyindan-5-yl)-N-(4-fluorobenzyl)-N-methyl-acetamidine (6.6 mg, 0.02 mmol) in DMF (0.2 mL). Agitate the mixture for 16 hours then add polystyrene trisamine resin (Argonaut Technologies, 3.7 mmol/g) (100 mg, 0.37 mmol) and agitate for a further 24 hours. Filter the mixture to deliver a 0.01 M solution of the title compound. MS (m/e): 577 ($M^+$).

Examples 4-2 through 4-37 are prepared essentially as Example 4-1.

| Ex. # | Compound Name | MS (m/e) |
|---|---|---|
| 4-2 | 2',6'-Dichlorobiphenyl-4-carboxylic acid (R)-(6-(1-((4-fluorobenzyl)methylamino)ethylideneamino)-2(R)-hydroxyindan-1-yl)amide | 542 ($M^+$) |
| 4-3 | 2-Methylbiphenyl-4-carboxylic acid (R)-(6-(1-((4-fluorobenzyl)methylamino)ethylideneamino)-2(R)-hydroxyindan-1-yl)amide | 522 ($M^+$) |
| 4-4 | 2'-Chlorobiphenyl-4-carboxylic acid (R)-(6-(1-((4-fluorobenzyl)methylamino)ethylideneamino)-2(R)-hydroxyindan-1-yl)amide | 542 ($M^+$) |
| 4-5 | 4'-Trifluoromethylbiphenyl-4-carboxylic acid (R)-(6-(1-((4-fluorobenzyl)methylamino)ethylideneamino)-2(R)-hydroxyindan-1-yl)amide | 576 ($M^+$) |
| 4-6 | 3-Chloro-2',4'-difluorobiphenyl-4-carboxylic acid (R)-(6-(1-((4-fluorobenzyl)methylamino)ethylideneamino)-2(R)-hydroxyindan-1-yl)amide | 578 ($M^+$) |
| 4-7 | 2'-Trifluoromethylbiphenyl-4-carboxylic acid (R)(6-(1-((4-fluorobenzyl)methylamino)ethylideneamino)-2(R)-hydroxyindan-1-yl)amide | 576 ($M^+$) |
| 4-8 | 4'-Methylbiphenyl-4-carboxylic acid (R)-(6-(1-((4-fluorobenzyl)methylamino)ethylideneamino)-2(R)-hydroxyindan-1-yl)amide | 522 ($M^+$) |
| 4-9 | 6-(2,6-Difluorophenyl)pyridine-3-carboxylic acid (R)-(6-(1-((4-fluorobenzyl)methylamino)ethylideneamino)-2(R)-hydroxyindan-1-yl)amide | 545 ($M^+$) |
| 4-10 | 6-(2-Methylphenyl)pyridine-3-carboxylic acid (R)-(6-(1-((4-fluorobenzyl)methylamino)ethylideneamino)-2(R)-hydroxyindan-1-yl)amide | 523 ($M^+$) |
| 4-11 | 3',4'-Difluorobiphenyl-4-carboxylic acid (R)-(6-(1-((4-fluorobenzyl)methylamino)ethylideneamino)-2(R)-hydroxyindan-1-yl)amide | 544 ($M^+$) |
| 4-12 | 3',5'-Dimethylbiphenyl-4-carboxylic acid (R)-(6-(1-((4-fluorobenzyl)methylamino)ethylideneamino)-2(R)-hydroxyindan-1-yl)amide | 536 ($M^+$) |
| 4-13 | 4-Cyclohexylphenyl-1-carboxylic acid (R)-(6-(1-((4-fluorobenzyl)methylamino)ethylideneamino)-2(R)-hydroxyindan-1-yl)amide | 514 ($M^+$) |
| 4-14 | 3'-Cyanobiphenyl-4-carboxylic acid (R)-(6-(1-((4-fluorobenzyl)methylamino)ethylideneamino)-2(R)-hydroxyindan-1-yl)amide | 533 ($M^+$) |
| 4-15 | 3',5'-Difluorobiphenyl-4-carboxylic acid (R)-(6-(1-((4-fluorobenzyl)methylamino)ethylideneamino)-2(R)-hydroxyindan-1-yl)amide | 544 ($M^+$) |
| 4-16 | 3'-Fluorobiphenyl-4-carboxylic acid (R)-(6-(1-((4-fluorobenzyl)methylamino)ethylideneamino)-2(R)-hydroxyindan-1-yl)amide | 526 ($M^+$) |
| 4-17 | 2',4'-Difluorobiphenyl-4-carboxylic acid (R)-(6-(1-((4-fluorobenzyl)methylamino)ethylideneamino)-2(R)-hydroxyindan-1-yl)amide | 544 ($M^+$) |
| 4-18 | 2',3'-Dichlorobiphenyl-4-carboxylic acid (R)-(6-(1-((4-fluorobenzyl)methylamino)ethylideneamino)-2(R)-hydroxyindan-1-yl)amide | 576 ($M^+$) |
| 4-19 | 4'-Chlorobiphenyl-4-carboxylic acid (R)-(6-(1-((4-fluorobenzyl)methylamino)ethylideneamino)-2(R)-hydroxyindan-1-yl)amide | 542 ($M^+$) |

-continued

| Ex. # | Compound Name | MS (m/e) |
|---|---|---|
| 4-20 | 3'-Chlorobiphenyl-4-carboxylic acid (R)-(6-(1-((4-fluorobenzyl)methylamino)ethylideneamino)-2(R)-hydroxyindan-1-yl)amide | 542 (M+) |
| 4-21 | 4-Trifluoromethylphenyl-1-carboxylic acid (R)-(6-(1-((4-fluorobenzyl)methylamino)ethylideneamino)-2(R)-hydroxyindan-1-yl)amide | 500 (M+) |
| 4-22 | 4-Methylphenyl-1-carboxylic acid (R)-(6-(1-((4-fluorobenzyl)methylamino)ethylideneamino)-2(R)-hydroxyindan-1-yl)amide | 446 (M+) |
| 4-23 | 3',5'-Dichlorobiphenyl-4-carboxylic acid (R)-(6-(1-((4-fluorobenzyl)methylamino)ethylideneamino)-2(R)-hydroxyindan-1-yl)amide | 576 (M+) |
| 4-24 | 2',4',6'-Trimethylbiphenyl-4-carboxylic acid (R)-(6-(1-((4-fluorobenzyl)methylamino)ethylideneamino)-2(R)-hydroxyindan-1-yl)amide | 550 (M+) |
| 4-25 | 6-(4-fluoro-2-methylphenyl)pyridine-3-carboxylic acid (R)-(6-(1-((4-fluorobenzyl)methylamino)ethylideneamino)-2(R)-hydroxyindan-1-yl)amide | 541 (M+) |
| 4-26 | 5-(2,4-Difluorophenyl)pyridine-2-carboxylic acid (R)-(6-(1-((4-fluorobenzyl)methylamino)ethylideneamino)-2(R)-hydroxyindan-1-yl)amide | 545 (M+) |
| 4-27 | 2'-Fluoro-4'-trifluoromethylbiphenyl-4-carboxylic acid (R)-(6-(1-((4-fluorobenzyl)methylamino)ethylideneamino)-2(R)-hydroxyindan-1-yl)amide | 594 (M+) |
| 4-28 | 4-(Pyrrol-1-yl)phenyl-1-carboxylic acid (R)-(6-(1-((4-fluorobenzyl)methylamino)ethylideneamino)-2(R)-hydroxyindan-1-yl)amide | 597 (M+) |
| 4-29 | 6-Methylpyridine-3-carboxylic acid (R)-(6-(1-((4-fluorobenzyl)methylamino)ethylideneamino)-2(R)-hydroxyindan-1-yl)amide | 447 (M+) |
| 4-30 | 4-Cyanophenyl-1-carboxylic acid (R)-(6-(1-((4-fluorobenzyl)methylamino)ethylideneamino)-2(R)-hydroxyindan-1-yl)amide | 457 (M+) |
| 4-31 | 3,2',6'-Trifluorobiphenyl-4-carboxylic acid (R)-(6-(1-((4-fluorobenzyl)methylamino)ethylideneamino)-2(R)-hydroxyindan-1-yl)amide | 562 (M+) |
| 4-32 | 3,2',6'-Trifluorobiphenyl-4-carboxylic acid (R)-(6-(1-((4-fluorobenzyl)methyl)amino)ethylideneamino)-2(R)-hydroxyindan-1-yl)amide | 541 (M+) |
| 4-33 | 2'-Methylbiphenyl-4-carboxylic acid (R)-(6-(1-((4-fluorobenzyl)methylamino)ethylideneamino)-2(R)-hydroxyindan-1-yl)amide | 522 (M+) |
| 4-34 | 2'-Methoxybiphenyl-4-carboxylic acid (R)-(6-(1-((4-fluorobenzyl)methylamino)ethylideneamino)-2(R)-hydroxyindan-1-yl)amide | 538 (MH+) |
| 4-35 | 3,2'-Difluorobiphenyl-4-carboxylic acid (R)-(6-(1-((4-fluorobenzyl)methylamino)ethylideneamino)-2(R)-hydroxyindan-1-yl)amide | 544 (MH+) |
| 4-36 | 6'-Fluoro-2'-trifluoromethylbiphenyl-4-carboxylic acid (R)-(6-(1-((4-fluorobenzyl)methylamino)ethylideneamino)-2(R)-hydroxyindan-1-yl)amide | 594 (MH+) |

EXAMPLE 5-1

6-Cyanopyridine-3-carboxylic acid (R)-(6-(1-((4-fluorobenzyl)methylamino)ethylideneamino)-2(R)-hydroxyindan-1-yl)amide

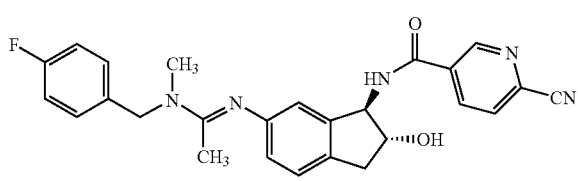

Dissolve equimolar amounts of N'-(3-amino-2-hydroxy-indan-5-yl)-N-(4-fluorobenzyl)-N-methylacetamidine (229 mg, 0.70 mmol) and 6-cyano-3-carboxypyridine (0.70 mmol, 103 mg) in anhydrous DMF (4.0 mL). Add triethylamine (0.487 mL, 3.50 mmol), followed by benzotriazol-1-yloxytris-dimethylamino phophonium hexafluorophosphate (296 mg, 0.70 mmol). Allow the reaction to stir at room temperature for 0.5 hours. Dilute the reaction with water (100 mL) and extract with EtOAc (3×50 mL). Dry the combined organic layers over MgSO$_4$, filter and concentrate. Dissolve the crude reaction product in THF (5.0 mL). Add hydroxide resin (BIO-RAD AG 1-X8 resin, 20-50 mesh—washed with water), 1 M NaOH, MeOH, ether and dried in vacuo) until solution is basic and stir at ambient temperature for 24 h. Filter the reaction, wash with additional THF, evaporate onto silica gel and purify by flash column chromatography with EtOAc/Hexanes to give 253 mg (79%) of the title compound as a white solid. MS (m/e): 458 (M+).

Examples 5-2 through 5-8 are prepared essentially as Example 5-1.

| Ex. # | Compound Name | MS (m/e) |
|---|---|---|
| 5-2 | 3,5-Difluorobiphenyl-4-carboxylic acid (R)-(6-(1-((4-fluorobenzyl)methylamino)ethylideneamino)-2(R)-hydroxyindan-1-yl)amide | 544.2 (M+) |
| 5-3 | 4-(Thien-3-yl)phenyl-1-carboxylic acid (R)-(6-(1-((4-fluorobenzyl)methylamino)ethylideneamino)-2(R)-hydroxyindan-1-yl)amide | 514.1 (M+) |
| 5-4 | 6-Trifluoromethylpyridine-3-carboxylic acid (R)-(6-(1-((4-fluorobenzyl)methylamino)ethylideneamino)-2(R)-hydroxyindan-1-yl)amide | 501.1 (M+) |
| 5-5 | 3-Fluoro-2'-trifluoromethylbiphenyl-4-carboxylic acid (R)-(6-(1-((4-fluorobenzyl)methylamino)ethylideneamino)-2(R)-hydroxyindan-1-yl)amide | 594.1 (M+) |
| 5-6 | 2-Fluoro-4-trifluoromethylphenyl-1-carboxylic acid (R)-(6-(1-((4-fluorobenzyl)methylamino)ethylideneamino)-2(R)-hydroxyindan-1-yl)amide | 518.4 (M+) |
| 5-7 | 2'-Chloro-3-fluorobiphenyl-4-carboxylic acid (R)-(6-(1-((4-fluorobenzyl)methylamino)ethylideneamino)-2(R)-hydroxyindan-1-yl)amide | 560.2 (M+) |
| 5-8 | 5-Phenylpyrazine-2-carboxylic acid (R)-(6-(1-((4-fluorobenzyl)methylamino)ethylideneamino)-2(R)-hydroxyindan-1-yl)amide | 510.3 (M+) |

EXAMPLE 6-1

6-(2-Chlorophenyl)pyridine-3-carboxylic acid (R)-(6-(1-((4-fluorobenzyl)methylamino)ethylideneamino)-2(R)-hydroxyindan-1-yl)amide

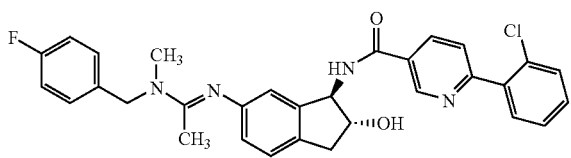

Dissolve N'-(3(R)-amino-2(R)-hydroxyindan-5—yl)-N-(4-fluorobenzyl)-N-methylacetamidine (42 mg, 0.13 mmol) and 6-(2-chlorophenyl)pyridine-3-carboxylic acid (103 mg, 0.70 mmol) in anhydrous DMF (2.5 mL). Add triethylamine (0.178 mL) followed by benzotriazol-1-yloxytris-dimethylamino phophonium hexafluorophosphate (54 mg, 0.13 mmol). Allow the reaction to stir at room temperature until completion. Dilute the reaction with water (100 mL) and extract with EtOAc. Dry the combined organic layers over MgSO₄, filter, and concentrate. Purify by flash column chromatography with CHCl₃/MeOH mixtures to yield 276 mg (35.7%) of solid title compound is isolated. MS (m/e): 543.0 (M+).

Examples 6-2 through 6-4 are prepared essentially as Example 6-1.

| Ex. # | Compound Name | MS (m/e) |
|---|---|---|
| 6-2 | 6-(2,4-Difluorophenyl)pyridine-3-carboxylic acid (R)-(6-(1-((4-fluorobenzyl)methylamino)ethylideneamino)-2(R)-hydroxyindan-1-yl)amide | 545.1 (M+) |
| 6-3 | 4-Iodophenyl-1-carboxylic acid (R)-(6-(1-((4-fluorobenzyl)methylamino)ethylideneamino)-2(R)-hydroxyindan-1-yl)amide | 558.0 (M+) |
| 6-4 | 6-(Thien-3-yl)pyridine-3-carboxylic acid (R)-(6-(1-((4-fluorobenzyl)methylamino)ethylideneamino)-2(R)-hydroxyindan-1-yl)amide | 515.4 (MH+) |

EXAMPLE 7-1

4-(Pyridin-3-yl)phenyl-1-carboxylic acid (R)-(6-(1-((4-fluorobenzyl)methylamino)ethylideneamino)-2(R)-hydroxyindan-1-yl)amide

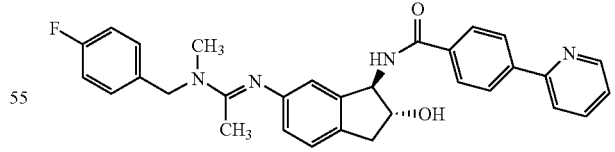

Combine 4-iodophenyl-1-carboxylic acid (R)-(6-(1-((4-fluorobenzyl)methylamino)ethylideneamino)-2(R)-hydroxyindan-1-yl)amide (0.131 g, 0.235 mmol), 2-(tributylstannyl)pyridine (0.129 g, 0.352 mmol) and tetrakis(triphenylphosphine)palladium(0) (0.406 g, 0.352 mmol) in dioxane at 80° C. Heat with stirring until completion. Remove the solvent by evaporation. Dilute the residue with Ethyl acetate and stir with an equal volume of saturated potassium fluoride for 3 hours. Filter the solution through a pad of celite. Separate the organic layer from the aqueous layer and dry over magnesium sulfate. Remove the organic solvent by evaporation and purify via flash chromatography with dichloromethane and methanol to yield 0.035 g (30%) of the title compound as solid material. MS (m/e): 509.2 (M+).

EXAMPLE 8-1

2',4',6'-Trifluorobiphenyl-4-carboxylic acid (R)-(6-(1-((4-fluorobenzyl)methylamino)ethylideneamino)-2(R)-hydroxyindan-1-yl)amide

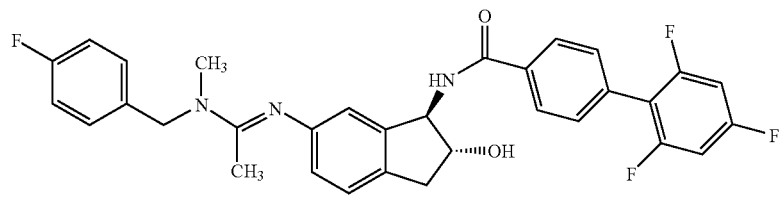

Combine 2',4',6'-trifluorobiphenyl-4-carboxylic acid (66 mg, 0.26 mmol), EDC (53 mg, 0.28 mmol) and N-hydroxysuccinimide (0.33 mg, 0.28 mmol) in dichloromethane and stir until completion. Wash the solution with 1 N hydrochloric acid. The organic layer is dried over magnesium sulfate and concentrated. The residue is combined with N'-(3(R)-amino-2(R)-hydroxyindan-5-yl)-N-(4-fluorobenzyl)-N-methylacetamidine (42 mg, 0.13 mmol) in dichloromethane and stirred until completion of reaction. The solvent is removed by evaporation and the residue purified via flash chromatography with dichloromethane and methanol to yield 37 mg of the title compound. MS (m/e): 562.0 (M+).

EXAMPLE 9-1

3,4'-Difluorobiphenyl-4-carboxylic acid (R)-(6-(1-((4-fluorobenzyl)methylamino)ethylideneamino)-2(R)-hydroxyindan-1-yl)amide

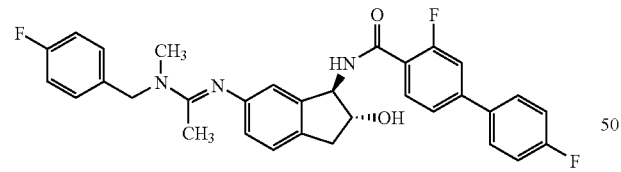

Stir a mixture of 3,4'-difluorobiphenyl-4-carboxylic acid (160 mg, 0.684 mmol), N-hydroxysuccinimmide (79 mg, 0.684 mmol) and DCC (141 mg, 0.684 mmol) in 15 mL of methylene chloride at rt for 2 h. Combine (6-(1-((4-fluorobenzyl)methylamino)ethylideneamino)-2(R)-hydroxyindan-1-yl)carbamic acid tert-butyl ester (256 mg. 0.62 mmol) with TFA (2 mL) at 0° C. and stir for 2 hr. Evaporate TFA under reduced pressure. Dissolve the residue in methylene chloride and evaporate to dryness-repeat this process three times. Add 5 mL of methylene chloride and 1 mL of triethylamine. Add this resulting solution to the above mixture and stir at rt for 12 h.

Pour the mixture into methylene chloride, wash with water, dry with Na$_2$SO$_4$, and concentrate. Purify the residue by column chromatography (silica gel, 3% MeOH in CH$_2$Cl$_2$) to give 199 mg of the title compound as a white solid (55% yield).

$^1$H NMR (CDCl3) δ 8.21 (1H, t, J=8.4 Hz), 7.58 (2H, dd, J=8.8 and 4.8 Hz), 7.32 (1H, d, J=13.2 Hz), 7.26-7.23 (2H, m), 7.19-7.12 (3H, m), 7.04 (2H, t, J=8.8 Hz), 6.68 (1H, s), 6.66 (1H, s), 5.32 (1H, t, J=5.2 Hz), 4.82-4.72 (1H, m), 4.64 (2H, s), 4.56(1H, q, J=6.4 Hz), 3.32(1H, dd, J=15.6 and 8.0 Hz), 3.00(3H, s), 2.96(1H, dd, J=15.2 and 8.4 Hz), 1.96 (3H, s). MS 544 (MH$^+$).

Examples 9-2 through 9-6 are prepared essentially as Example 9-1.

| Ex. # | Compound Name | MS (m/e) |
|---|---|---|
| 9-2 | 4'-Fluorobiphenyl-4-carboxylic acid (R)-(6-(1-((4-fluorobenzyl)methylamino)ethylideneamino)-2(R)-hydroxyindan-1-yl)amide | 526 (MH$^+$) |
| 9-3 | 4'-Fluoro-2'-methoxybiphenyl-4-carboxylic acid (R)-(6-(1-((4-fluorobenzyl)methylamino)ethylideneamino)-2(R)-hydroxyindan-1-yl)amide | 556 (MH$^+$) |
| 9-4 | 2',6'-Difluorobiphenyl-4-carboxylic acid (R)-(6-(1-((4-fluorobenzyl)methylamino)ethylideneamino)-2(R)-hydroxyindan-1-yl)amide | 544 (MH$^+$) |
| 9-5 | 2'-Fluorobiphenyl-4-carboxylic acid (R)-(6-(1-((4-fluorobenzyl)methylamino)ethylideneamino)-2(R)-hydroxyindan-1-yl)amide | 526.1 (MH$^+$) |
| 9-6 | 3,2',4'-Trifluorobiphenyl-4-carboxylic acid (R)-(6-(1-((4-fluorobenzyl)methylamino)ethylideneamino)-2(R)-hydroxyindan-1-yl)amide | 562 (M + 1) |

EXAMPLE 10-1

4-Bromophenyl-1-carboxylic acid (R)-(6-(1-((furan-2-ylmethyl)methylamino)ethylideneamino)-2(R)-hydroxyindan-1-yl)amide

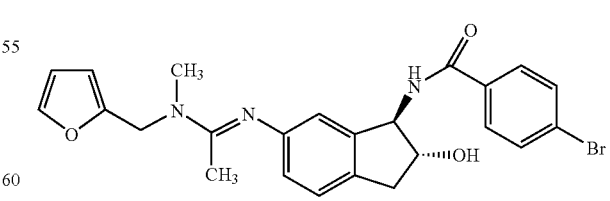

To a mixture of thioacetamide (10.04 g, 133.64 mmol) and K$_2$CO$_3$ (45.80 g, 331.38 mmol) in 100 ml THF at 0° C. add phthaloyl chloride (28.49 g, 140.32 mmol) dropwise. Raise the reaction temperature to 25° C. after 2 hours and allow it to stir for an additional 2 hours before cooling the reaction mixture to 0° C. again. Quench the reaction by adding 125 mL of ice water dropwise. Extract the reaction mixture with EtOAc (2×). Dry the organic layer with MgSO$_4$ and remove the solvent in vacuo to yield 3.7 g of N-thioacetyl-isoindole-1,3-dione as a crude reddish solid.

Dissolve N-methylfurfurylamine (117.2 mg, 1.05 mmol) in 20 ml Et$_2$O at 25° C. To this add N-thioacetyl-isoindole-1,3-dione (294.4 mg, 1.43 mmol) and allow to stir for 24 hours. Add MeOTf(181.7 mg, 1.11 mmol) to the reaction mixture and allow to stir for an additional 23 hours. Decant the Et$_2$O from the oil and triturate the oil with Et$_2$O-repeat this three times. Remove any excess Et$_2$O from the oily residue in vacuo to obtain 320.4 mg of crude thioimidate as an oil. Dissolve this crude product (161.1 mg, 0.483 mmol) in 10 mL pyridine and add N-(6-amino-2-hydroxyindan-1-yl)-4-bromobenzamide (107.5 mg, 0.310 mmol). Allow the reaction to stir at 25° C. for 22 hours. Remove the solvent in vacuo and partition the residue between CH$_2$Cl$_2$ and saturated aqueous NaHCO$_3$. Dry the organic layer with MgSO$_4$. Filter and remove the solvent in vacuo to give 146.2 mg of crude product. Purify via Biotage chromatography (1% MeOH/EtOAc) to afford 63.6 mg of the title compound as an off-white solid (43%). MS (m/e): 483 (M+1).

EXAMPLE 11-1

4-Bromophenyl-1-carboxylic acid (R)-(6-(1-((4-fluorobenzyl)amino)ethylideneamino)-2(R)-hydroxyindan-1-yl)amide

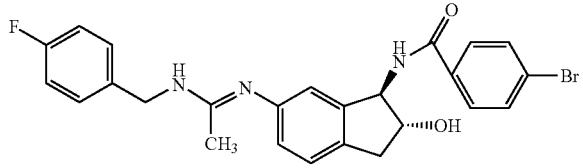

Step a) Combine (6-amino-2-hydroxyindan-1-yl)carbamic acid tert-butyl ester (3.7 g, 14.0 mmol) with 10 mL of TFA at 0° C. Stir the mixture for 1 h and evaporate to dryness. Add to the residue 6.5 mL of triethylamine and 30 mL of methylene chloride. Combine this mixture slowly with a solution of 4-bromobenzoic acid benzotriazole-1-yl ester in 15 mL of methylene chloride at 0° C. Stir the resulting mixture for 12 h at rt. Filter to give 3.4 g (70% yield) of N-(6-amino-2-hydroxyindan-1-yl)-4-bromobenzamide as white solid. MS 348 (MH$^+$).

Step b) Add acetyl chloride (9.28 g, 118 mmol) to a mixture of triethylamine (16.0 g, 158 mmol) and 4-fluorobenzylamine (9.90 g, 78.8 mmol) in 200 mL of ethyl acetate at 0° C. and stir for 12 hours. Add 100 mL of water to the mixture. Extract aqueous layer with ethyl acetate (3×100 mL). Combine organic layers and wash with brine then dry over anhydrous Na$_2$SO$_4$ Remove solvent under reduced pressure to give N-(4-fluorobenzyl)acetamide (13.5 gm) in 100% yield as a yellow oil. Add NaH (6.5 g, 162 mmol) to N-(4-fluorobenzyl)-acetamide (13.5 g, 80.8 mmol) in 200 mL of tetrahydrofuran at 0° C. and stir for 4 hours. Then add methyl iodide (22.9 g, 161.6 mmol) to the above mixture and stir for 12 hours. Pour mixture into 200 mL of water. Extract aqueous layer with methylene chloride (3×200 mL). Combine organic layers and wash with brine then dry over anhydrous Na$_2$SO$_4$. Remove solvent under reduced pressure. Purify the residue by column chromatography (silica gel, 5% acetone in hexanes, 50% acetone in hexanes) to give N-(4-fluorobenzyl)-N-methylacetamide (9.1 gm) in 64% yield as a yellow oil. Add Lawesson reagent (20.3 g, 50.3 mmol) to N-(4-fluorobenzyl)-N-methylacetamide (9.1 g, 50.3 mmol) in 200 mL of toluene and heat to 100° C. for three hours. Remove solvent under reduced pressure. Purify the residue with a column chromatography (silica gel, 2% methylene chloride in hexanes, 100% methylene chloride) to give N-(4-fluorobenzyl)-N-methylthioacetamide (5.6 g) 56.5% as a yellow solid: MS 198 (MH$^+$).

Step c) Add Lawesson reagent (1.8 g, 3.6 mmol) to N-(4-fluorobenzyl)acetamide (0.9 g, 5.4 mmol) in 50 mL of toluene and heat to 80° C. for 12 hours. Remove solvent under reduced pressure. Purify the residue by column chromatography (silica gel, Acetone: Hexane=20:80) to give a mixture. Wash with ether and discard insoluble solid impurities by filtration. Remove solvent under reduced pressure to give N-(4-fluorobenzyl)-thioacetamide (0.7 gm) in 71% as a yellow solid: MS 184 (MH$^+$).

Step d) Add methyl trifluoromethanesulfonate (0.190 g, 1.16 mmol) to a solution of N-(3-fluorobenzyl)thioacetamide (0.106 g, 0.580 mmol) in 10 mL of CH$_2$Cl$_2$ at room temperature. Stir the mixture for 30 minutes and remove the solvent under reduced pressure. Dissolve the residue in 5 mL of pyridine. Then add the trifluoroacetic acid salt of N-(6-amino-2-hydroxyindan-1-yl)-4-bromobenzamide to the solution. Stir for three hours. Remove pyridine under reduced pressure. Purify the residue with column chromatography (silica gel/Hexanes:Acetone =7:3, 1:1) to give 40 mg of the title compound in 14% yield as a white solid: MS 496(MH$^+$).

Examples 11-2 through 11-17 are prepared essentially as Example 11-1.

| Ex. # | Compound Name | MS (m/e) |
|---|---|---|
| 11-2 | 4-Bromophenyl-1-carboxylic acid (R)-(6-(1-((3-fluorobenzyl)amino)ethylideneamino)-2(R)-hydroxyindan-1-yl)amide | 496 (MH$^+$) |
| 11-3 | 4-Bromophenyl-1-carboxylic acid (R)-(6-(1-((1,3-benzodioxol-5-ylmethyl)amino)ethylideneamino)-2(R)-hydroxyindan-1-yl)amide | 522 (MH$^+$) |
| 11-4 | 4-Bromophenyl-1-carboxylic acid (R)-(6-(1-((4-methoxybenzyl)amino)ethylideneamino)-2(R)-hydroxyindan-1-yl)amide | 508 (MH$^+$) |
| 11-5 | 4-Bromophenyl-1-carboxylic acid (R)-(6-(1-((3-methoxybenzyl)amino)ethylideneamino)-2(R)-hydroxyindan-1-yl)amide | 508 (MH$^+$) |
| 11-6 | 4-Bromophenyl-1-carboxylic acid (R)-(6-(1-((2-methoxybenzyl)amino)ethylideneamino)-2(R)-hydroxyindan-1-yl)amide | 508 (MH$^+$) |
| 11-7 | 4-Bromophenyl-1-carboxylic acid (R)-(6-(1-((4-fluorobenzyl)methylamino)ethylideneamino)-2(R)-hydroxyindan-1-yl)amide | 510 (MH$^+$) |
| 11-8 | 4-Bromophenyl-1-carboxylic acid (R)-(6-(1-((2-(4-fluorophenyl)ethyl)amino)ethylideneamino)-2(R)-hydroxyindan-1-yl)amide | 510 (MH$^+$) |
| 11-9 | 4-Bromophenyl-1-carboxylic acid (R)-(6-(1-((2-(2-fluorophenyl)ethyl)amino)ethylideneamino)-2(R)-hydroxyindan-1-yl)amide | 510 (MH$^+$) |
| 11-10 | 4-Bromophenyl-1-carboxylic acid (R)-(6-(1-((2-(4-methoxyphenyl)ethyl)amino)ethylideneamino)-2(R)-hydroxyindan-1-yl)amide | MS 522 (MH$^+$) |
| 11-11 | 4-Bromophenyl-1-carboxylic acid (R)-(6-(1-((2-(3-fluorophenyl)ethyl)amino)ethylideneamino)-2(R)-hydroxyindan-1-yl)amide | 510 (MH$^+$) |
| 11-12 | 4-Bromophenyl-1-carboxylic acid (R)-(6-(1-((2-(2-methoxyphenyl)ethyl)amino)ethylideneamino)-2(R)-hydroxyindan-1-yl)amide | 522 (MH$^+$) |

-continued

| Ex. # | Compound Name | MS (m/e) |
|---|---|---|
| 11-13 | 4-Bromophenyl-1-carboxylic acid (R)-(6-(1-((2-(3-methoxyphenyl)ethyl)amino)ethylideneamino)-2(R)-hydroxyindan-1-yl)amide | 522 (MH+) |
| 11-14 | 4-Bromophenyl-1-carboxylic acid (R)-(6-(1-((2-(2,3-dimethoxyphenyl)ethyl)amino)ethylideneamino)-2(R)-hydroxyindan-1-yl)amide | 552 (MH+) |
| 11-15 | 4-Bromophenyl-1-carboxylic acid (R)-(6-(1-((2-(1,3-benzodioxol-5-yl)ethyl)amino)ethylideneamino)-2(R)-hydroxyindan-1-yl)amide | 536 (MH+) |
| 11-16 | 4-Bromophenyl-1-carboxylic acid (R)-(6-(1-((2-(4-fluorophenyl)ethyl)amino)ethylideneamino)-2(R)-hydroxyindan-1-yl)amide | 524 (MH+) |
| 11-17 | 4-Bromophenyl-1-carboxylic acid (R)-(6-(1-((2-(2-methoxyphenyl)ethyl)amino)ethylideneamino)-2(R)-hydroxyindan-1-yl)amide | 536 (MH+) |

EXAMPLE 12-1

Biphenyl-4-carboxylic acid (R)-(6-(1-((4-fluorobenzyl)methylamino)ethylideneamino)-2(R)-hydroxyindan-1-yl)amide Combine (6-amino-2-hydroxyindan-1-yl)carbamic acid tert-butyl ester (1.5 g, 5.68 mmol) with 5 mL of TFA at 0° C. Stir the mixture for 1 h and then evaporate to dryness. Added 3.0 mL of triethylamine and 30 mL of methylene chloride the residue. To this mixture, add a solution of biphenyl-4-carboxylic acid 2,5-dioxo-pyrrolidin-1-yl ester (1.76 g, 5.96 mmol) in 15 mL of methylene chloride. Stir the resulting mixture for 12 h. Evaporate solvent and purify the residue by a column chromatography (silica gel/MeOH: $CH_2Cl_2$=9:1) to give 1.88 g (96% yield) of biphenyl-4-carboxylic acid (6-amino-2-hydroxyindan-1-yl)amide; MS 345 (MH+).

Add methyl trifluoromethanesulfonate (0.290 g, 1.76 mmol) to a solution of N-(4-fluorobenzyl)thioacetamide (0.2 gm, 1.0 mmol) in 5 mL of $CH_2Cl_2$ at room temperature. Stir the mixture for 30 minutes and remove the solvent under reduced pressure. Dissolve the residue in 5 mL of pyridine. Then add biphenyl-4-carboxylic acid (6-amino-2-hydroxyindan-1-yl)amide to the solution. Stir for 12 hours. Remove pyridine under reduced pressure. Purify the residue with column chromatography (silica gel/Hexanes: Acetone =7:3, 1:1) to give 78 mg of the title compound in 35% yield as a white solid: $^1H$ NMR (DMSO-$d_6$) δ 8.78 (1H, d, J=8.8 Hz), 8.04 (2H, d, J=8.8 Hz), 7.79 (2H, d, J=8.4 Hz), 7.74 (2H, dd, J=7.4, 1.6 Hz), 7.50 (2H, t, J=8.0 Hz), 7.41 (1H, t, J=7.2 Hz), 7.28 (2H, dd, J=8.8, 6.6 Hz), 7.14 (2H, t, J=8.8 Hz), 7.04 (1H, t, J=7.6 Hz), 6.78 (1H, d, J=7.2 Hz), 6.37 (1H, s), 5.33 (1H, d, J=5.6 Hz), 5.27 (1H, t, J=7.6 Hz), 4.59 (2H, s), 4.45 (1H, q, J=6.0 Hz), 3.10 (1H, dd, J=14.8, 7.2 Hz), 2.90 (3H, s), 2.68 (1H, dd, J=14.8, 7.2 Hz), 1.88 (3H, s); MS 508 (MH+).

Examples 12-2 through 12-7 are prepared essentially as Example 12-1.

| Ex. # | Compound Name | MS (m/e) |
|---|---|---|
| 12-2 | Biphenyl-4-carboxylic acid (R)-(6-(1-((3-methoxybenzyl)methylamino)ethylideneamino)-2(R)-hydroxyindan-1-yl)-amide | 520 (MH+) |
| 12-3 | Biphenyl-4-carboxylic acid (R)-(6-(1-((3,4-difluorobenzyl)methylamino)ethylideneamino)-2(R)-hydroxyindan-1-yl)amide | 526 (MH+) |
| 12-4 | Biphenyl-4-carboxylic acid (R)-(6-(1-((2-(4-fluorophenyl)ethyl)amino)ethylideneamino)-2(R)- | 508 (MH+) |
| 12-5 | Biphenyl-4-carboxylic acid (R)-(6-(1-((2-(2-methoxyphenyl)ethyl)amino)ethylideneamino)-2(R)-hydroxyindan-1-yl)amide | 520 (MH+) |
| 12-6 | Biphenyl-4-carboxylic acid (R)-(6-(1-((2-(2-fluorophenyl)ethyl)amino)ethylideneamino)-2(R)-hydroxyindan-1-yl)amide | 508 (MH+) |
| 12-7 | Biphenyl-4-carboxylic acid (R)-(6-(1-((2-(4-fluorophenyl)ethyl)methylamino)ethylideneamino)-2(R)-hydroxyindan-1-yl)amide | 522 (MH+) |

EXAMPLE 13-1

Biphenyl-4-carboxylic acid (R)-(7-(1-((4-fluorobenzyl)methylamino)ethylideneamino)-2(R)-hydroxy-1,2,3,4-tetrahydronaphthalen-1-yl)amide

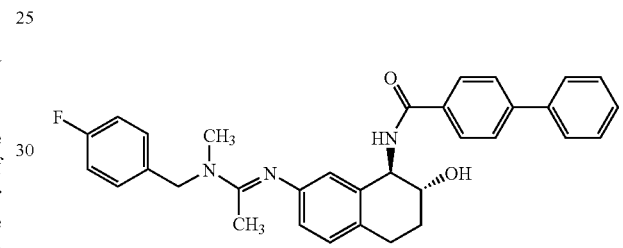

Stir a mixture of 1-amino-7-nitro-1,2,3,4-tetrahydronaphthalen-2-ol (500 mg, 2.40 mmol) and 1N NaOH (4.8 mL, 4.8 mmol) in a mixture of 50 mL of toluene and 50 mL of water for 30 minutes. Added biphenyl-4-carbonyl chloride (570 mg, 2.64 mmol) slowly and stir for four hours at room temperature. Remove the solid by filtration, and wash with toluene. Evaporate solvent under reduced pressure. Biphenyl-4-carboxylic acid (2-hydroxy-7-nitro-1,2,3,4-tetrahydro-naphthalen-1-yl)-amide is obtained in 54% as a white solid: $^1H$ NMR (DMSO-$d_6$) δ 8.87 (1H, d, J=8.4 Hz), 8.03 (2H, d, J=8.4 Hz), 7.99 (2H, d, J=7.6 Hz), 7.79 (2H, d, J=8.4 Hz), 7.74 (2H, d, J=8.4 Hz), 7.50 (2H, t, J=7.2 Hz), 7.43(2H, t, J=6.8 Hz), 5.22 (1H, d, J=4.4 Hz), 5.11 (1H, t, J=7.6 Hz), 3.95-4.01 (1H, m), 2.87-3,07(2H, m), 2.08-2.15 (1H, m), 1.81-1.94 (1H, m); MS 389(MH+). The above compound (0.25 g, 0.64 mmol) is reduced in 10 mL of DMF with 48 mg of 10% Pd-C at room temperature under 60 psi (414 kPa) for overnight to form biphenyl-4-carboxylic acid (7-amino-2-hydroxy-1,2,3,4-tetrahydro-naphthalen-1-yl)-amide, obtained in 96% as a yellow oil. MS 359 (MH+).

Add methyl trifluoromethanesulfonate (0.150 g, 0.915 mmol) to a solution of N-4-fluorobenzyl-N-methylthioacetamide (0.145 g, 0.736 mmol) in 10 mL of $CH_2Cl_2$ at room temperature. Stir the mixture for 30 minutes and remove the solvent under reduced pressure. Then add biphenyl-4-carboxylic acid (7-amino-2-hydroxy-1,2,3,4-tetrahydro-naphthalen-1-yl)-amide (0.22 g, 0.61 mmol) followed by 5 mL of pyridine. Stir the resulting mixture for 12 h. After evaporate pyridine, purify the residue by column chromatography (silica gel, 5% MeOH in $CH_2Cl_2$) to give 10 mg of the title compound in 2.6% yield as a light yellow solid: $^1H$ NMR (CDCl$_3$) δ 7.89 (2H, d, J=8.0 Hz), 8.66 (2H, d, J=8.4 Hz), 7.61 (2H, d, J=7.2 Hz), 7.47 (2H, t, J=7.6 Hz), 7.39 (1H, t, J=7.6 Hz), 7.21 (1H, dd, J=6.0, 8.8 Hz), 6.98-7.05 (3 B, m), 6.72 (1H, s), 6.62 (1H, dd, J=2.0, 8.4 Hz), 6.56 (1H, d, J=7.2 Hz), 5.22 (1H, t, J=7.6 Hz), 4.60 (2H, s), 3.98-4.04 (2H, m), 3.41 (11H, t, J=6.0 Hz), 2.96 (3H, s), 2.85 (2H, t, J=4.8 Hz), 2.15-2.21 (2H, m), 1.87-1.95 (1H, m), 1.92 (3H, s), 1.60-1.64 (1H, m); MS 522 (MH$^+$).

EXAMPLE 14-1

3-Fluorobiphenyl-4-carboxylic acid (R)-(6-(1-((3,4-difluorobenzyl)methylamino)ethylideneamino)-2(R)-hydroxyindan-1-yl)amide

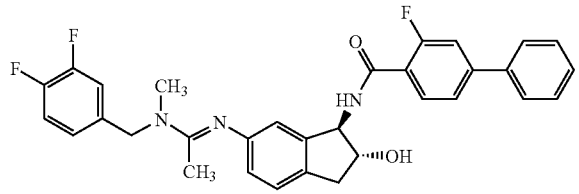

Beginning with 3,4-difluorobenzylamine, N-(3,4-difluorobenzyl)-N-methyl-thioacetamide is prepared essentially as Step b, Example 11-1, and is obtained in 66% yield as a yellow solid: MS 216 (MH$^+$).

Add methyl trifluoromethanesulfonate (0.750 g, 3.49 mmol) to a solution of N-(3,4-difluorobenzyl)-N-methylthioacetamide (0.145 g, 0.736 mmol) in 10 mL of CH$_2$Cl$_2$ at room temperature. Stir the mixture for 30 minutes and remove the solvent under reduced pressure. Then add (6-amino-2-hydroxyindan-1-yl)-carbamic acid t-butyl ester (0.78 g, 2.97 mmol) followed by 5 mL of pyridine. The resulting mixture is stirred for 12 h. After pyridine is evaporated, the residue is purified by column chromatograph (silica gel, 3% MeOH in CH$_2$Cl$_2$) to give 0.98 g of (6-(1-((3,4-difluorobenzyl)-methyl-amino)-ethylideneamino)-2-hydroxyindan-1-yl)-carbamic acid tert-butyl ester as a white solid: MS 446 (MH$^+$).

Add 5 mL of trifluoroacetic acid to (R)-(6-(1-((3,4-difluorobenzyl)methylamino)ethylideneamino)-2(R)-hydroxyindan-1-yl)carbamic acid tert-butyl ester (180 mg, 4.04 mmol) and stir for 30 minutes. Remove solvent under reduced pressure. Dissolve the residue in 15 mL of CH$_2$Cl$_2$. Then add 3-fluorobiphenyl-4-carboxylic acid 2,5-dioxopyrrolidin-1-yl ester (150 mg, 4.79 mmol) and triethylamine (0.6 mL, 4.0 mmol) to the solution and stir for 12 hours. Pour the mixture into methylene chloride, wash with water, dry with Na$_2$SO$_4$, and then concentrate. Purify the residue by column chromatography (silica gel, 3% MeOH in CH$_2$Cl$_2$) to give 35 mg of the title compound as a white solid in 16% yield: $^1$H NMR (CD$_3$OD) δ 7.88 (2H, t, J=8.0 Hz), 7.7 (2H, d, J=8.4 Hz), 7.60 (2H, dd, J=8.0, 1.2 Hz), 7.47-7.55 (3H, m), 7.43-7.47 (1H, m), 7.21-7.32 (2H, m), 7.18 (1H, d, J=8.0 Hz), 7.11-7.14 (1H, m), 6.71 (2H, dd, J=10.0, 1.2 Hz), 5.47 (1H, d, J=6.8 Hz), 4.69 (2H, s), 4.54 (1H, q, J=7.2 Hz), 4.54 (1H, q, J=6.4 Hz), 3.29 (1H, q, J=7.2 Hz), 3.07 (3H, s), 2.88 (1H, q, J=7.8 Hz), 1.99 (3H, s); MS 544 (MH$^+$).

EXAMPLE 15-1

2'-Trifluoromethylbiphenyl-4-carboxylic acid (R)-(6-(1-((4-fluorobenzyl)methylamino)ethylideneamino)indan-1-yl)amide

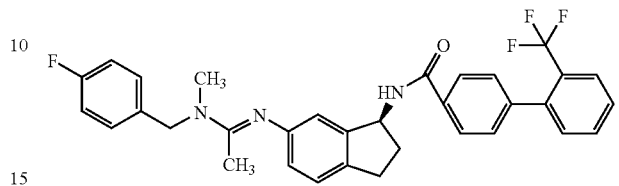

Combine 1-aminoindan (1.0 g, 8.1 mmol) with 6.6 mL of fuming HNO$_3$ at −10° C. Stir the resulting mixture for 30 min, pour into ice and then stir for 30 min. Collect the solid, wash with water, and dry to afford 0.614 g (42%) of product. Mix with di-tert-butyldicarbonate (0.929 g, 4.26 mmol) in THF. Combine the mixture with saturated K$_2$CO$_3$ aqueous solution to adjust to pH11. Stir for 8 h, pour into CH$_2$Cl$_2$, wash with water, dry, and concentrate. Dissolve the residue into a 1:1 mixture of ether and hexane, then keep at −10° C. overnight. Collect the solid and dry to give 0.57 g (59%) of (6-Nitro-indan-1-yl)carbamic acid tert-butyl ester. $^1$H NMR (CDCl$_3$) d 8.16 (1H, br s), 8.11 (1H, dd, J=8.4 and 2.0 Hz), 7.34 (1H, d, J=8.4 Hz), 5.25 (1H, q, J=8.8 Hz), 4.78 (1 h, br d, J=6.4 Hz), 3.08-2.00 (1H, m), 2.96-2.78 (1H, m), 2.72-2.62 (1H, m), 1.93-1.83 (1H, m), 1.51 (9H, s).

Add KBH$_4$ (1.59 g, 29.4 mmol) slowly to a mixture of (6-nitro-indan-1-yl)carbamic acid tert-butyl ester (1.17 g, 4.2 mmol) and CuCl (1.25 g, 12.6 mmol) in 50 mL of methanol at 0° C. over 15 min. Stir the mixture for 1 h and then pass through a Florisil pad. Evaporate the THF and dissolve the solid in EtOAc. Wash the mixture with water, dry, and concentrate to afford 0.76 g (73%) of (6-aminoindan-1-yl)carbamic acid tert-butyl ester. $^1$H NMR (CDCl$_3$) d 6.99 (1H, d, J=8.0 Hz), 6.65 (1H, s), 6.56 (1H, dd, J=8.0 and 2.0 Hz), 5.09 (1H, q, J=8.0 Hz), 4.70 (1H, br d, J=7.2 Hz), 3.60 (2H, s), 2.86-2.79 (1H, m), 2.75-2.67 (1H, m), 2.58-2.47 (1H, m), 1.78-1.69 (1H, m), 1.48 (3H, s). 2.86-2.79 (1H, m), 2.75-2.67 (1H, m), 2.58-2.47 (1H, m), 1.78-1.69 (1H, m), 1.48 (3H, s).

Add MeI (0.623 g, 4.4 mmol) to a solution of N-4-fluorobenzyl-N-methylthioacetamide (0.662 g, 3.4 mmol) in 10 mL of ether at rt. Stir the mixture for 3 h and evaporate the ether under vacuum. Add (6-aminoindan-1-yl)carbamic acid tert-butyl ester (0.7 g, 2.28 mmol) followed by 5 mL of pyridine. Stir the resulting mixture for 12 h. Evaporate pyridine and purify the residue by column chromatography (silica gel, 3% MeOH in CH$_2$Cl$_2$) to give 1.26 g of (6-(1-((4-fluorobenzyl)methylamino)ethylideneamino)indan-1-yl)carbamic acid tert-butyl ester as a light yellow solid; MS 412 (MH$^+$); $^1$H NMR (CD$_3$OD) d 7.35-7.29 (2H, m), 7.18-7.10 (3H, m), 6.70 (1H, s), 6.65 (1H, d, J=7.6 Hz), 5.06 (1H, t, J=6.8 Hz), 4.69 (2H, s), 3.05 (3H, s), 2.97-2.91 (1H, m), 2.84-2.77 (1H, m), 2.55-2.48 (1H, m), 1.97 (3H, s), 1.52 (9H, s).

Stir a mixture of 2'-trifluoromethylbiphenyl-4-carboxylic acid (100 mg, 0.376 mmol), N-hydroxysuccinimmide (43 mg, 0.376 mmol) and DCC (77 mg, 0.376 mmol) in 15 mL of methylene chloride at rt for 2 h. Combine (6-(1-((4-fluorobenzyl)methylamino)ethylideneamino)indan-1-yl) carbamic acid tert-butyl ester (129 mg. 0.313 mmol) with TFA (2 mL) at 0° C. and stir for 2 hr. Evaporate TFA under reduced pressure. Dissolve the residue in methylene chloride and evaporate to dryness; repeat this three times. Add 5 mL of methylene chloride and 1 mL of triethylamine. Add this resulting solution to the above mixture and stir at rt for 12 h. Pour the mixture into methylene chloride, wash with water, dry with $Na_2SO_4$, and concentrate. Purify the residue by column chromatography (silica gel, 3% MeOH in $CH_2Cl_2$) to give 82 mg of the title compound as a white solid (47% yield).

MS 560 (MH$^+$); $^1$H NMR (CDCl$_3$) d 7.83 (2H, d, J=8.0 Hz), 7.75 (1H, d, =7.6 Hz), 7.56 (1H, t, J=7.2 Hz), 7.49 (1H, t, J=8.0 Hz), 7.40 (2H, d, J=8.0 Hz), 7.31 (1 H, d, J=8.0 Hz), 7.26-7.21 (3H, m), 7.15 (1H, d, J=7.6 Hz), 7.02 (2H, t, J=8.8 Hz), 6.75 (1H, s), 6.64 (1H, d, J=7.2 Hz), 5.67 (1H, q, J=7.6 Hz), 4.61 (2H, q, J=10.0 Hz), 2.97 (3H, s), 2.94-2.83 (1H, m), 2.75-2.68 (1H, m), 2.00-1.70 (4H, br s), 1.69-1.58 (1H, m).

Examples 15-2 through 15-7 are prepared essentially as Example 15-1.

| Ex. # | Compound Name | MS (m/e) |
|---|---|---|
| 15-2 | 3,5-Difluorobiphenyl-4-carboxylic acid (R)-(6-(1-((4-fluorobenzyl)methylamino)ethylideneamino)indan-1-yl)amide | 528 (MH$^+$) |
| 15-3 | 2'-Fluorobiphenyl-4-carboxylic acid (R)-(6-(1-((4-fluorobenzyl)methylamino)ethylideneamino)indan-1-yl)amide | 510 (MH$^+$) |
| 15-4 | 2',6'-Difluoromethylbiphenyl-4-carboxylic acid (R)-(6-(1-((4-fluorobenzyl)methylamino)ethylideneamino)indan-1-yl)amide | 528 (MH$^+$) |
| 15-5 | Biphenyl-4-carboxylic acid (R)-(6-(1-((4-fluorobenzyl)methylamino)ethylideneamino)indan-1-yl)amide | 492 (MH$^+$) |
| 15-6 | 3-Fluorobiphenyl-4-carboxylic acid (R)-(6-(1-((4-fluorobenzyl)methylamino)ethylideneamino)indan-1-yl)amide | 510 (MH$^+$) |
| 15-7 | 3,2'-Difluorobiphenyl-4-carboxylic acid (R)-(6-(1-((4-fluorobenzyl)methylamino)ethylideneamino)indan-1-yl)amide | 528 (MH$^+$) |

Example P-1

Biphenyl-4-carboxylic acid (R)-(6-(1-((4-fluorobenzyl)methylamino)ethylideneamino)-2(R)-hydroxyindan-1-yl)amide hemihydrate Add 21.8 L of methanol to 2.86 kg of biphenyl-4-carboxylic acid (R)-(6-(1-((4-fluorobenzyl)methylamino)ethylideneamino)-2(R)-hydroxyindan-1-yl)amide solvate. Pass the solution through a carbon impregnated filter and rinse the filter with 24 L of methanol. Add 5.7 kg of water to the solution over 35 min followed by 15 g of Biphenyl-4-carboxylic acid (R)-(6-(1-((4-fluorobenzyl)methylamino)ethylideneamino)-2(R)-hydroxyindan-1-yl)amide hemihydrate seed crystals. After 20 min, add 1.15 kg of water followed by 15 g of seed crystals. After 1 h, add another 1.15 kg of water over 30 min followed by 15 g of seed crystals. After 10 min, add 3.4 kg of water over 1 h and stir the slurry at room temperature for 1 h and at 0° C. for 45 min. Collect the solid by filtration, rinse with a cold solution of 11.4 L of methanol and 2.9 L of water, and dry to afford 2.19 kg of the title compound as a white solid.

Example P-2

Biphenyl-4-carboxylic acid (R)-(6-(1-((4-fluorobenzyl)methylamino)ethylideneamino)-2(R)-hydroxyindan-1-yl)amide hemihydrate Dissolve biphenyl-4-carboxylic acid (R)-(6-(1-((4-fluorobenzyl)methylamino)ethylideneamino)-2(R)-hydroxyindan-1-yl)amide solvate (2.0 g) in methanol (24 mL) at 20-23° C. Add water (5 mL) to the solution, followed by hemihydrate seed crystals (20 mg). Stir the mixture for 2 h at 20-23° C., then cool to 0-5° C. Filter the mixture, wash with a solution of methanol (8 mL) and water (2 mL), and dry at 50-60° C. under vacuum for 16 h to give 1.66 g of the title compound.

Example P-3

Biphenyl-4-carboxylic acid (R)-(6-(1-((4-fluorobenzyl)methylamino)ethylideneamino)-2(R)-hydroxyindan-1-yl)amide hemihydrate Combine a solution of 6-(1-((4-Fluorobenzyl)methylamino)ethylideneamino)-2-hydroxy-1-biphenylaminoindane acetonitrile solvate (101 g) and methanol (1.2 L) with Darco G-60 (5 g). After stirring for 15-30 min at 15-25° C., filter the mixture and rinse the filtered solids with methanol (0.4 L). Add water (0.4 L) to the combined filtrate, rinse, and add hemihydrate seed crystals (1.5 g). Stir the mixture 2-3 h at 15-25° C., then cool to 0-5° C. and stir another 90 min. Filter the mixture, wash with a 0-5° C. solution of methanol (0.8 L) and water (0.2 L), and dry at 47-53° C. under vacuum for 20 h to give 88.7 g of the title compound.

The compounds of the present invention can be administered alone or in the form of a pharmaceutical composition, that is, combined with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be Formulated and administered in the form of their pharmaceutically acceptable salts, for purposes of stability, convenience, solubility, and the like. In practice, the compounds of Formula I are usually administered in the form of pharmaceutical compositions, that is, in admixture with pharmaceutically acceptable carriers or diluents.

Thus, the present invention provides pharmaceutical compositions comprising a compound of Formula I and a pharmaceutically acceptable diluent. The present invention also provides suitable packaging, including a label, containing the pharmaceutical compositions comprising a compound of Formula I.

The compounds of Formula I can be administered by a variety of routes. In effecting treatment of a patient afflicted with disorders described herein, a compound of Formula I can be administered in any form or mode which makes the compound bioavailable in an effective amount, including oral and parenteral routes. For example, compounds of Formula I can be administered orally, by inhalation, subcutaneously, intramuscularly, intravenously, transdermally, intranasally, rectally, occularly, topically, sublingually, buccally, and the like. Oral administration is generally preferred for treatment of the disorders described herein.

One skilled in the art of preparing Formulations can readily select the proper form and mode of administration depending upon the particular characteristics of the compound selected, the disorder or condition to be treated, the stage of the disorder or condition, and other relevant circumstances. (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and nontoxic in the amounts used.

For the purpose of oral and parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of Formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical Formulations may contain a concentration of the Formula I or its pharmaceutical salt from about 0.1 to about 10% w/v (weight per unit volume).

The compounds of Formula I are agonists of the M-1 muscarinic receptors. Moreover the compounds of Formula I are selective agonists of that particular muscarinic receptor. The compounds of the present invention possess particularly useful properties related to their bioavailability, pharmacokinetics, safety, and efficacy. Muscarinic agonists, including their subtype binding profile, can be identified by the methods that are well known in the art.

In one embodiment, the present invention provides methods of treating disorders associated with muscarinic receptors, comprising: administering to a patient in need thereof an effective amount of a compound of Formula I. Thus, the present invention contemplates the various disorders described to be treated herein and others which can be treated by such agonists as are appreciated by those skilled in the art.

A number of the disorders which can be treated by muscarinic agonists are known according to established and accepted classifications, while others are not. For example, cognition is a complicated and sometimes poorly defined phenomenon. It is, however, widely recognized that cognition includes various "domains." These domains include short term memory, long term memory, working memory, executive function, and attention.

It is understood that the compounds of the present invention are useful for treatment of disorders characterized by a deficit in any of the cognitive domains listed above or in other aspects of cognition. Thus the term "cognitive disorders" is meant to encompass any disorder characterized by a deficit in one or more cognitive domain, including but not limited to short term memory, long term memory, working memory, executive function, and attention.

One cognitive disorder to be treated by the present invention is age-related cognitive decline. This disorder is not well defined in the art, but includes decline in the cognitive domains, particularly the memory and attention domains, which accompany aging. Another cognitive disorder is mild cognitive impairment. Again, this disorder is not well defined in the art, but involves decline in the cognitive domains, and is believed to represent a group of patients the majority of which have incipient Alzheimer's disease. Another cognitive disorder is cognitive impairment associated with schizophrenia. The relationship between cognitive disturbances and other symptoms of schizophrenia is not clearly understood at present. It has been observed that some people experience cognitive problems much before they develop positive symptoms, while others acquire cognitive deterioration after the first episode and with subsequent relapses. Yet another cognitive disorder is chemotherapy-induced cognitive impairment. People who undergo cancer chemotherapy may experience a decline in cognitive function and this decline can be long lasting. Also, a wide variety of insults, including stroke, ischemia, hypoxia, inflammation, infectious processes and cognitive deficits subsequent to cardiac bypass surgery and grafting, stroke, cerebral ischemia, spinal cord trauma, head trauma, perinatal hypoxia, fetal alcohol syndrome, cardiac arrest, and hypoglycemic neuronal damage, vascular dementia, multi-infarct dementia, amylotrophic lateral sclerosis, chemotherapy, and multiple sclerosis can result in cognitive deficits as a sequella which can be treated according to the present invention.

Where the disorders which can be treated by muscarinic agonists are known according to established and accepted classifications, these classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

In particularly preferred embodiments, the present invention provides methods of treating disorders selected from the group consisting of: cognitive disorders (including age-related cognitive disorder, mild cognitive impairment, cognitive impairment associated with schizophrenia, and chemotherapy-induced cognitive impairment), ADHD, mood disorders (including depression, mania, bipolar disorders), psychosis (in particular schizophrenia and schizophreniform disorder), dementia (including Alzheimer's disease, AIDS-induced dementia, vascular dementia, and dementia lacking distinctive histology), Parkinson's disease, Huntington's Chorea, pain (including acute pain and chronic pain), xerostomia (dry mouth), Lewy body disease (including diffuse Lewy body disease), aphasia (including primary aphasia and primary aphasia syndromes), aphasia (including primary aphasia and primary aphasia syndromes), hypotensive syndromes, and chronic colitis (including Crohn's disease), comprising: administering to a patient in need thereof an effective amount of a compound of Formula I. That is, the present invention provides for the use of a compound of Formula I or pharmaceutical composition thereof for the treatment disorders associated with muscarinic receptors.

It is recognized that the terms "treatment" and "treating" are intended to include improvement of the symptomatology associated with each of the disorders associated with muscarinic receptors described herein. Also, it is also recognized that one skilled in the art may affect the disorders by treating a patient presently afflicted with the disorders or by prophylactically treating a patient believed to be susceptible to such disorders with an effective amount of the compound of Formula I. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms, and is intended to include prophylactic treatment of such disorders.

It is understood that the present invention includes adjunctive treatment of the disorders described herein. More specifically, the compounds of Formula I are useful to treat disorders in which a cognitive deficit is one of the symptoms in combination with a wide variety of other therapeutic agents, in particular, in combination with AMPA potentiators; with typical and atypical antipsychotics, including olanzapine; with a variety of agents such as mGluR agonists, with NMDA antagonists, with IL 1-6 inhibitors, with other cholinergics, including cholinesterase inhibitors, such as tacrine and donepezil, and compounds that inhibit amyloid protein processing, including inhibitors of amyloid precursor protein processing and antibodies directed against amyloid proteins; with antidepressants, including SSRIs and SNRIs such as fluoxetine, paroxetine, and venlafaxine; and with anxiolytic agents; etc. It is believed that the combinations above are synergistically beneficial providing efficacy at doses that are a small fraction of those required to produce the same effect with the individual components.

In accordance with the adjunctive treatments, described above, the present invention also provides a product containing a compound of Formula I and one or more therapeutic agents selected from the group consisting of AMPA potentiators; typical and atypical antipsychotics, including olanzapine; mGluR agonists; NMDA antagonists; IL 1-6 inhibitors; cholinesterase inhibitors, such as tacrine and donepezil; compounds that inhibit amyloid protein processing, including inhibitors of amyloid precursor protein processing and antibodies directed against amyloid proteins; antidepressants, including SSRIs and SNRIs such as fluoxetine, paroxetine, and venlafaxine; and anxiolytic agents as a combined preparation for simultaneous, separate or sequential administration in the treatment of disorders in which a cognitive deficit is one of the symptoms. In another embodiment the present invention also provides for the use of a compound of Formula I together with one or more therapeutic agents selected from AMPA potentiators; typical and atypical antipsychotics, including olanzapine; mGluR agonists; NMDA antagonists; IL 1-6 inhibitors; cholinesterase inhibitors, such as tacrine and donepezil; compounds that inhibit amyloid protein processing, including inhibitors of amyloid precursor protein processing and antibodies directed against amyloid proteins; antidepressants, including SSRIs and SNRIs such as fluoxetine, paroxetine, and venlafaxine; and anxiolytic agents for the manufacture of a medicament as a combined preparation for simultaneous, separate or sequential administration in the treatment of disorders in which a cognitive deficit is one of the symptoms.

As used herein, the term "simultaneous, separate or sequential administration" means that the two or more therapeutic agents are administered within a time frame which ensures that all of the therapeutic agents will provide some therapeutic activity at a particular point in time. That is to say, the therapeutic activities should at least overlap to some degree although they need not be coterminus.

As used herein, the term "patient" includes a mammal which is afflicted with one or more disorders associated with muscarinic receptors. It is understood that guinea pigs, dogs, cats, rats, mice, horses, cattle, sheep, pigs, and humans are examples of animals within the scope of the meaning of the term.

As used herein, the term "effective amount" of a compound of Formula I refers to an amount, that is, the dosage which is effective in treating the disorders described herein.

An effective amount can be readily determined by the attending diagnostician, as one skilled in the art, by the use of conventional techniques and by observing results obtained under analogous circumstances. In determining an effective amount, the dose of a compound of Formula I, a number of factors are considered by the attending diagnostician, including, but not limited to: the compound of Formula I to be administered; the co-administration of other therapies, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of Formula I is expected to vary from about 0.01 milligram per kilogram of body weight per day (mg/kg/day) to about 50 mg/kg/day, and preferable from 0.1 milligram per kilogram of body weight per day (mg/kg/day) to about 20 mg/kg/day. More preferred amounts can be determined by one skilled in the art.

Of the disorders to be treated according to the present invention a number are particularly preferred. Particularly preferred disorders include the treatment of cognitive disorders (particularly mild cognitive impairment and cognitive impairment associated with schizophrenia), Alzheimer's disease, and psychosis, including schizophrenia.

A number of preclinical laboratory animal models have been described for the disorders described herein.

EXAMPLE A

Radial Arm Maze

The delayed non-match to sample task has been used to study the effect of drugs on memory retention (Pussinen, R. and Sirvio, J. *J of Psychopharm* 13: 171-179(1999); Staubli, U., et al. *Proc Natl Acad Sci* 91: 777-781(1994)) in the eight arm radial maze.

Well-trained rats were allowed to retrieve food rewards from four randomly selected arms of the maze (sampling phase). Some time later, the rats were exposed to eight open arms and were tested for their ability to remember and avoid the arms they had previously entered to obtain food. Re-entry into an arm that was baited during the sampling session was counted as a reference error, whereas entry into the same arm more than once during the retention session was counted as working error. The total (reference +working) number of errors made during the retention test increases with increasing delay periods. For example, young male rats made 0.66 (+0.4) errors at a 1 minute delay, 2 (+0.5) errors at a one hour delay, and 3.95 (+0.2) errors at a seven hour delay (observations of this lab).

Male Sprague-Dawley rats were individually housed and maintained on a 12 h light-dark cycle (lights on at 6 am). The rats were given free access to water and maintained at 85% of their free-feeding weight by supplemental feedings of Purina Lab Chow.

The rats were initially trained to search for food at the end of each of the eight arms. Once the rats had reached the criteria of no more than two errors (i.e. entering the same arm more than once during a session) on three consecutive days, a delay of one minute was imposed between the fourth and the fifth arm choices. This training ensured that the rats were thoroughly familiar with the procedural aspects of the task before any drugs were administered. Once stable performance had been obtained on the delay task (i.e. no more than one error was made on three consecutive days), drug and vehicle tests commenced using a seven hour delay period. A novel set of arms was baited each day for each rat and the maze was thoroughly cleaned during the delay period.

During the sampling session, each rat was placed on the center platform with access to all eight arms of the maze blocked. Four of the eight arms were randomly selected and baited with food. The gates of the baited arms were raised and the rat was allowed five minutes to obtain the food at the end of each of the four arms. As soon as the rat had obtained the food, it was removed, administered vehicle or various doses of compounds, and placed back in its home cage. Seven hours later (retention session), the rat was placed back onto the center platform with access to all eight arms blocked. The four arms that were previously baited during the sampling session, were baited and the gates to all eight arms were raised. The rat was allowed five minutes to obtain the remaining four pieces of food. An entry into a non-baited arm or a re-entry into a previously visited arm was counted as an error. Significance (p<0.05) was determined using a repeated measure ANOVA followed by a Dunnett's test for comparison with control.

In order to compare test compounds with standards, scopolamine and tacrine were administered s.c. immediately after the sampling phase. The effects of scopolamine, a known amnesic, were tested after a three-hour delay, whereas the effect of tacrine, a cholinesterase inhibitor used in the treatment of Alzheimer's disease was tested after a six-hour delay. Scopolamine disrupted retention after a three-hour delay in a dose-related fashion. Tacrine significantly improved retention after a six-hour delay at 10, but not at 3 mg/kg.

EXAMPLE B

Acquisition in the Radial Maze 8-Arm Radial Maze Acquisition

A prominent early feature of Alzheimer's disease (AD) symptomology is a pronounced deficit in declarative memory (R. W. Parks, R. F. Zec & R. S. Wilson (Eds.), *Neuropsychology of Alzheimer's disease and other dementias*. NY: Oxford University Press pp. 3-80 (1993).

As the disease progresses, other domains of cognition become severely affected as well. Among the brain regions affected early in the progression of Alzheimer's disease is the hippocampus, which is a critical neural substrate for declarative memory. Differences in the pattern of hippocampal neuronal loss in normal aging and Alzheimer's disease. *Lancet,* 344: 769-772(1994). One behavioral test that is often used to assess hippocampal function in animal models is the 8-arm radial maze (Olton D. S. The radial arm maze as a tool in behavioral pharmacology. Physiology & Behavior, 40: 793-797 (1986)).

Lesions or pharmacological blockade of the hippocampus disrupt performance of this task. Moreover, aged animals generally show deficits in this task (Porsolt R. D., Roux S. & Wettstein J. G. Animal models of dementia. Drug Development Research, 35: 214-229(1995)).

In this test of spatial learning and memory, a hungry rat is placed in the center of the maze and allowed to traverse the maze in search of food located at the end of each runway arm. In this version of the maze, the rat learns a win-shift strategy in which a visited arm is not replaced. Therefore, the most efficient foraging strategy is to visit each arm once. The version of the maze also taps into general learning processes as the rat is naïve to the maze on day one of the four day experiment.

Upon arrival, male Sprague Dawley®, rats were individually housed in a regular light-cycle colony room and allowed to acclimate for at least 4 days prior to testing. Each rat was reduced to and maintained at 85% of their target body weight throughout the experiment. Proper body weight was maintained by adjusting the allotment of lab chow based on a combination of age and the rat's daily bodyweight reading.

A session began with an individual rat being placed into the hub of the maze and then all guillotine doors were raised, allowing free access to all areas of the maze. A food hopper was located at the end of each of the 8 runway arms and a single food pellet was placed in each food hopper. Each daily session terminated when either all 8 food-hoppers had been visited or when the rat timed out (15 min on Day 1: 5 min on Days 2-4). The number of arm entries was recorded. Errors were counted as repeat arm entries or failures to visit an arm in the session period. An animal was excluded from the study if it failed to visit at least one arm on Day 1, 2 arms on Day 2, and at least 4 arms on Days 3 & 4.

Each rat was pseudo-randomly assigned to either a vehicle or drug group and received the same treatment throughout the experimental period. Vehicle consisted of 5% acacia within sterile water. Injections were administered subcutaneously 20-30 minutes prior to each daily session.

In this acquisition task, vehicle-treated animals do not consistently show significant acquisition of maze learning as compared to the number of errors committed on Day 1. We have found that in compounds that facilitate acquisition of maze learning, the effects are often not observed until the fourth day of training. Therefore, results consisted of total Day 4 errors across treatment groups.

EXAMPLE C

Functional Mobilization of Intracellular Calcium

CHO cells expressing muscarinic subtypes (M1-M5) are grown as monolayers in DMEM:F-12 (3:1), 10% FBSnz, 20 mM HEPES, 1% pen/strep, 250 µg/mL G418 (GibcoBRL #10131-027). Cells are maintained under 95%/5% $O_2/CO_2$ and passaged every 3-4 days. Cells are plated 24 hours in advance of the assay at a density of 50,000/well and 48 hours in advance at a density of 25,000/well (100 µL/well) in Costar black-walled, clear-bottomed 96 well plates (Costar #3603). Cells are then incubated with minimum essential medium containing the cytoplasmic $Ca^{2+}$ indicator, Fluo-3 (1 mM Fluo mixed 1:1 with 20% pluronic acid, then diluted to 5 µM final concentration in growth and supplemented with 2.5 mM, 50 µL/well) at 37° C. in an environment containing 5% $CO_2$ for 60 minutes. Cells are washed twice with 100 µL/well of wash buffer containing Hanks Balanced Salt Solution (HBSS) without phenol red (1×) (GibcoBRL #14065-056), 20 mM HEPES (Sigma #P8761), and Probenecid (2.5 mM) (100×: 1:100). For the assay, 100 µL is added to each well (100 µL of 2×drug will be added by the FLIPR). Plates are washed three times using a LabSystems multidrop and residual buffer is removed. Plates are also blotted on paper towels to remove remaining compound.

Compounds are prepared 2×(100 µL of drug added to 100 µL of assay buffer present in the well) in assay buffer containing 2% DMSO, HBSS without phenol red (1×) (GibcoBRL #14065-056), 20 mM HEPES (Sigma #P8761), and Probenecid (2.5 mM) (100×: 1:100).

The plates were then placed into a FLIPR instrument (fluorometric imaging plate reader system, Molecular Devices, Sunnyvale, Calif.) to monitor cell fluorescence ($\lambda_{EX}$=488 nm, $\lambda_{EM}$=540 nm) before and after the addition of compounds.

The selectivity of the M1 agonists are evaluated by screening across other muscarinic receptor subtypes (M3 and M5) in a similar manner in both the agonist and antagonist mode. Compounds are also sreened across a number of protein targets as well as the structurally related G protein-coupled receptor (GPCR) targets to insure selectivity for the M1 receptor.

EXAMPLE D

Functional GTP Binding

Cell Culture: CHO cells transfected with human M1-M5 receptors were grown either in suspension or in monolayer. For suspension cultures cells were grown in roller bottles with constant agitation at 37° C. and 5% $CO_2$ using Dulbecco's modified Eagles medium/F-12 (3:1) culture medium supplemented with 5% fetal bovine serum, 50 µg/ml tobramycin, and 20 mM HEPES. Monolayer cultures were grown in T-225 flasks at 37° C. and 5% $CO_2$ in Dulbecco's modified Eagles medium supplemented with 10% fetal bovine serum and 100,000 U/liter of penicillin/streptomycin. Cells were harvested using trypsin-free dissociation media at 95% confluence and were collected by centrifugation and stored at 80° C. Cells stably expressing human muscarinic receptors were obtained from the National Institutes of Health.

Membrane Preparation: Cell pellets were thawed and resuspended in 20 volumes of 20 mM sodium phosphate buffer, pH 7.4, and were homogenized twice for 30 seconds at high speed using a Tissuemizer. Homogenates were centrifuged at 200 g for 15 min at 4° C. The supernatant was removed and reserved on ice. This procedure was repeated twice and the pooled supernatants were then centrifuged at 40,000 g for 45 min at 4° C. Membranes were suspended at 5 mg protein/ml and were stored at 80° C. Unless indicated otherwise in the figure legends, membranes from M1, M2, and M4 cells were prepared from cells grown in suspension, whereas those from M3 and M5 cells were from cells grown in monolayer. Receptor densities (pmol mg1 membrane protein) were 9.3, 0.7, 0.6, 0.9, and 4.8 for M1-M5 receptors, respectively.

Striatal tissue from male Sprague-Dawley rats was homogenized by hand in 10 volumes of 10 mM HEPES and 1 mM EGTA, pH 7.4, containing Complete protease inhibitor cocktail, 1 mM dithiothreitol, and 10% sucrose. The homogenate was diluted 6-fold and centrifuged at 1000 g for 10 min at 4° C. The supernatant was saved and the pellet rehomogenized and centrifuged as above. The combined supernatants were centrifuged at 11,000 g for 20 min. The resulting pellet was homogenized in 40 volumes of 10 mM HEPES and 1 mM EGTA, pH 7.4, containing 1 mM dithiothreitol and 1 mM $MgCl_2$, and was centrifuged at 27,000 g for 20 min. The resulting pellet was suspended in the same buffer at a protein concentration of 1.5 mg/ml and aliquots were frozen and stored at 80° C.

GTP$\gamma^{35}$S Binding: Assays were run in 20 mM HEPES, 100 mM NaCl, and 5 mM $MgCl_2$ at pH 7.4 in a final volume of 200 µl in 96-well Costar plates at 25° C. One hundred microliters of membrane preparation (25 µg protein per well for cell membranes and 9-15 µg per well for brain membranes) containing the appropriate concentration of GDP was added followed by addition of 50 µl of buffer ±agonists and antagonists being tested followed by 50 µl of GTP$\gamma^{35}$S to provide a final concentration in the assay of 200 pM for CHO membranes and 500 pM for brain membranes. For CHO membranes, 0.1 µM GDP was used for M1, M3, and M5 receptor assays, whereas 1 µM GDP was used for M2 and M4 assays. For brain membranes 0.1 µM GDP was used in assays carried out with anti-G$\alpha$q/11, whereas 50 µM GDP was used for assays using anti-G$\alpha$i(1-3) and anti-G$\alpha$o. CHO cell membranes were incubated for 30 min at 25° C. with agonists and antagonists followed by addition of GTPγ$^{35}$S and incubation for an additional 30 min. Brain membranes were incubated for 20 min at 25° C. with agonists and antagonists followed by addition of GTPγ$^{35}$S and incubation for an additional 60 min. Preincubation was employed to ensure that agonists and antagonists were at equilibrium during the labeling period.

To determine total membrane binding, 50 μl of suspended wheat germ agglutinin (WGA)-coated SPA beads was added. After 15 min, plates were centrifuged at 1000 g for 15 min and radioactivity was determined using a Wallac plate counter. For determining binding to specific G proteins, $^{35}$S-labeled membranes were solubilized for 30 min with 0.27% Nonidet P-40 (20 μl/well of a solution containing 1.5 ml of 10% Nonidet P-40 for every 3.5 ml assay buffer) followed by addition of desired antibody (10 μl/well) to provide a final dilution of 1/400 to 1/100 and incubation for an additional 60 min. Fify microliters of suspended anti-IgG-coated SPA beads was added per well, plates were incubated for 3 h, and then were centrifuged and radioactivity determined as above. Each bottle of WGA-coated SPA beads was suspended in 10 ml of assay buffer and each bottle of anti-IgG-coated SPA beads was suspended in 20 ml of assay buffer. Protein was determined using the bicinchoninic acid assay.

Materials: $^{35}$S-GTPγS (1000-1200 Ci/mmol), anti-rabbit-IgG and anti-mouse-IgG-coated SPA beads, and WGA-coated SPA beads were obtained from Amersham (Arlington Heights, Ill.). Rabbit anti-Gαq/11 and rabbit anti-Gαi(1-3) were from Santa Cruz Biotechnologies (Santa Cruz, Calif.). Mouse monoclonal anti-Gαo was from Chemicon (Temecula, Calif.). Oxotremorine M and pirenzepine were from Research Biochemicals Inc. (Natick, Mass.). 11-{[2-((Diethylamino)methyl)-1-piperidinyl]acetyl}-5,11-dihydro-6H-pyrido[2,3 b][1,4]benzodiazepin-6-one (AFDX 116) was synthesized at Eli Lilly. Complete protease inhibitor cocktail and 10% Nonidet P-40 were from Boehringer Mannheim (Indianapolis, Ind.).

The selectivity of the M1 agonists are evaluated by screening across other muscarinic receptor subtypes (M2 and M4) in both the agonist and antagonist mode. Compounds are also screened across a number of protein targets as wail as the structurally related G protein-coupled receptor (GPCR) targets to insure selectivity for the M1 receptor.

What is claimed is:

1. A compound of the Formula

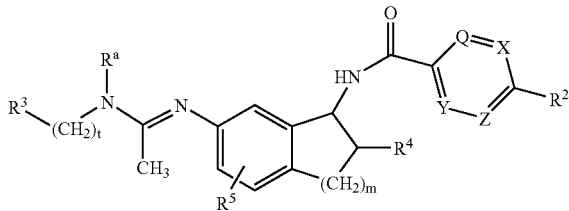

wherein
Q, X, Y, and Z are independently selected from the group consisting of CR$^1$ and N, provided that no more than two of Q, X, Y, and Z are N and at least two of Q, X, Y, and Z are CH; or Y is CH, Z is CH, and the moiety "Q=X" represents "S" to form a thiophene ring;

R$^1$ is independently at each occurrence selected from the group consisting of hydrogen, halogen, C$_1$-C$_4$ alkoxy, and C$_1$-C$_4$ alkyl;

R$^2$ is selected from the group consisting of halogen; C$_1$-C$_4$ alkoxy; C$_1$-C$_4$ alkyl; C$_3$-C$_8$ cycloalkyl; cyano; trifluoromethyl; pyridinyl optionally substituted with one to two substituents independently selected from the group consisting of halogen, C$_1$-C$_4$ alkoxy, and C$_1$-C$_4$ alkyl; thienyl optionally substituted with one substituent selected from the group consisting of halogen, C$_1$-C$_4$ alkoxy, and C$_1$-C$_4$ alkyl; phenyl optionally substituted with from one to three substituents independently selected from the group consisting of halogen, C$_1$-C$_4$ alkoxy, C$_1$-C$_4$ alkyl, trifluoromethyl, and cyano; and pyrrolyl optionally substituted with one to two substituents independently selected from the group consisting of halogen, C$_1$-C$_4$ alkoxy, and C$_1$-C$_4$ alkyl;

R$^3$ is selected from the group consisting of phenyl optionally substituted with one to three substituents independently selected from the group consisting of halogen, C$_1$-C$_4$ alkoxy, C$_1$-C$_4$ alkyl, trifluoromethyl, cyano, and nitro; naphthyl optionally substituted with one to three substituents independently selected from the group consisting of halogen, C$_1$-C$_4$ alkoxy, C$_1$-C$_4$ alkyl, trifluoromethyl, cyano, and nitro; heteroaryl optionally substituted with one or two substituents independently selected from the group consisting of halogen, C$_1$-C$_4$ alkoxy, and C$_1$-C$_4$ alkyl; or 1,3-benzodioxolyl optionally substituted with one substituent selected from the group consisting of halogen, C$_1$-C$_4$ alkoxy, and C$_1$-C$_4$ alkyl;

R$^4$ is selected from the group consisting of hydrogen, hydroxy, and fluoro;

R$^5$ is selected from the group consisting of hydrogen, halogen, C$_1$-C$_4$ alkoxy, and C$_1$-C$_4$ alkyl;

R$^a$ is selected from the group consisting of hydrogen and methyl;

t is one, two, or three; and m is one;

or pharmaceutically acceptable addition salts thereof.

2. A compound according to claim 1 wherein R$^a$ is methyl, R$^5$ is hydrogen, R$^4$ is hydroxy, t is one, m is one, and which has the trans stereochemistry at the 1- and 2-position shown below:

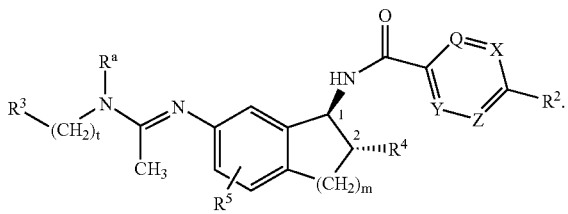

3. A compound according to claim 1 wherein Q, X, Y, and Z are each CH.

4. A compound according to claim 1 wherein R$^2$ is phenyl.

5. A compound according to claim 2 wherein R$^3$ is phenyl substituted once with halogen.

6. The compound biphenyl-4-carboxylic acid (R)-(6-(1-((4-fluorobenzyl)methylamino)ethylideneamino)-2(R)-hydroxyindan-1-yl)amide and the pharmaceutically acceptable salts thereof.

7. A pharmaceutical composition comprising a compound of claim 1 and one or more pharmaceutically acceptable carriers, excipients, or diluents.

8. A method of treating Alzheimer's disease, comprising: administering to a patient in need thereof an effective amount of a compound of claim 1.

9. A method of treating schizophrenia, comprising: administering to a patient in need thereof an effective amount of a compound of claim 1.

10. A pharmaceutical composition comprising a compound of claim 2 and one or more pharmaceutically acceptable carriers, excipients, or diluents.

11. A method of treating Alzheimer's disease, comprising: administering to a patient in need thereof an effective amount of a compound of claim 2.

12. A method of treating schizophrenia, comprising: administering to a patient in need thereof an effective amount of a compound of claim 2.

13. A method of treating Lewy body disease comprising: administering to a patient in need thereof an effective amount of a compound of claim 1.

14. A method of treating Lewy body disease comprising: administering to a patient in need thereof an effective amount of a compound of claim 2.

* * * * *